US010058559B2

(12) United States Patent
Strober et al.

(10) Patent No.: US 10,058,559 B2
(45) Date of Patent: Aug. 28, 2018

(54) TREATMENT OR PREVENTION OF AN INTESTINAL DISEASE OR DISORDER

(71) Applicant: The United States of America, as represented by the Secretary, Department of Health & Human Services, Washington, DC (US)

(72) Inventors: Warren Strober, Bethesda, MD (US); Ivan J. Fuss, Bethesda, MD (US); Tetsuya Takagawa, Rockville, MD (US); Atsushi Kitani, Rockville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 15/311,405

(22) PCT Filed: May 15, 2015

(86) PCT No.: PCT/US2015/031200
§ 371 (c)(1),
(2) Date: Nov. 15, 2016

(87) PCT Pub. No.: WO2015/176010
PCT Pub. Date: Nov. 19, 2015

(65) Prior Publication Data
US 2017/0079987 A1    Mar. 23, 2017

Related U.S. Application Data

(60) Provisional application No. 61/993,637, filed on May 15, 2014.

(51) Int. Cl.
| *A61K 31/5513* | (2006.01) |
| *G01N 33/68* | (2006.01) |
| *C12Q 1/6883* | (2018.01) |
| *A61K 45/06* | (2006.01) |
| *A61K 31/5377* | (2006.01) |
| *A61K 39/395* | (2006.01) |
| *C07K 16/40* | (2006.01) |

(52) U.S. Cl.
CPC ...... *A61K 31/5513* (2013.01); *A61K 31/5377* (2013.01); *A61K 39/3955* (2013.01); *A61K 45/06* (2013.01); *C07K 16/40* (2013.01); *C12Q 1/6883* (2013.01); *G01N 33/6893* (2013.01); *C07K 2317/76* (2013.01); *C12Q 2600/156* (2013.01); *C12Q 2600/158* (2013.01); *G01N 2333/91205* (2013.01); *G01N 2800/065* (2013.01); *G01N 2800/50* (2013.01)

(58) Field of Classification Search
CPC ............ A61K 31/5377; A61K 31/5513; A61K 39/3955; A61K 45/06; C07K 16/40; C07K 2317/76; C07K 2317/158; C12Q 2600/156; C12Q 2600/158; C12Q 1/6883; G01N 33/6893; G01N 2333/91205; G01N 2800/065; G01N 2800/50
See application file for complete search history.

(56) References Cited

U.S. PATENT DOCUMENTS

| 4,816,567 | A | 3/1989 | Cabilly et al. |
| 4,956,778 | A | 9/1990 | Naito et al. |
| 5,091,513 | A | 2/1992 | Huston et al. |
| 5,132,405 | A | 7/1992 | Huston et al. |
| 5,225,539 | A | 7/1993 | Winter et al. |
| 5,530,101 | A | 6/1996 | Queen et al. |
| 5,585,089 | A | 12/1996 | Queen et al. |
| 5,693,762 | A | 12/1997 | Queen et al. |
| 5,849,902 | A | 12/1998 | Arrow et al. |
| 5,859,205 | A | 1/1999 | Adair et al. |
| 7,947,468 | B2 | 5/2011 | Alessi et al. |
| 8,029,986 | B2 | 10/2011 | Meitinger et al. |
| 8,206,942 | B2 | 6/2012 | Alessi et al. |
| 8,354,420 | B2 | 1/2013 | Baker-Glenn et al. |
| 8,409,809 | B2 | 4/2013 | Meitenger et al. |
| 8,778,939 | B2 | 7/2014 | Nichols et al. |
| 8,791,130 | B2 | 7/2014 | Baker-Glenn et al. |
| 8,796,296 | B2 | 8/2014 | Baker-Glenn et al. |
| 8,802,674 | B2 | 8/2014 | Baker-Glenn et al. |
| 8,809,331 | B2 | 8/2014 | Baker-Glenn et al. |
| 8,815,882 | B2 | 8/2014 | Baker-Glenn et al. |
| 2003/0003469 | A1 | 1/2003 | Stinchcomb et al. |
| 2005/0042620 | A1 | 2/2005 | Hampel et al. |
| 2005/0196754 | A1 | 9/2005 | Drmanac et al. |
| 2014/0005183 | A1 | 1/2014 | Galatsis et al. |

FOREIGN PATENT DOCUMENTS

WO    WO-2011057204 A2    5/2011

OTHER PUBLICATIONS

Lewis PA and Manzoni C. Science Signaling. 5(207):pe2, 1-4. Jan. 17, 2012.*
A. Gardet et al: "LRRK2 Is Involved in the IFN-Response and Host Response to Pathogens", The Journal of Immunology, vol. 185, No. 9, Oct. 4, 2010 (Oct. 4, 2010), pp. 5577-5585.
International Search Report and Written Opinion of the International Searching Authority of corresponding International Patent Application PCT/US2015/031200 dated Jul. 15, 2015.
Aboul-Fadl, T., "Antisense Oligonucleotides: The State of the Art#", Current Medicinal Chemistry, 12, 763-771 (2005).
Bass, "The Short Answer", Nature, 411, 428-429 (2001).
Brummelkamp, et al., "A System for Stable Expression of Short Interfering RNAs in Mammalian Cells", Science 296: 550-553, (2002).

(Continued)

*Primary Examiner* — Robert S Landsman
(74) *Attorney, Agent, or Firm* — Locke Lord LLP; Nicholas J. DiCeglie, Jr.

(57) ABSTRACT

Disclosed are methods of treating or preventing an intestinal disease or disorder comprising administering to a subject a modulator of leucine rich repeat kinase 2 (LRRK2) in an amount effective to treat or prevent an intestinal disease or disorder and methods of determining the susceptibility or risk of a subject to develop an intestinal disease.

18 Claims, 15 Drawing Sheets

(56) References Cited

OTHER PUBLICATIONS

Davies, et al., "Comprehensive characterization and optimization of anti-LRRK2 (leucine-rich repeat kinase 2) monoclonal antibodies" Biochem. Journal (2013), Jul. 1, 453(1):101-113.
Delihas, N., et al., "Natural antisense RNA/target RNA interactions: possible models for antisense oligonucleotide drug design", Nature Biotechnology, vol. 15, Aug. 1997.
Deng, X., et al., "Characterization of a selective inhibitor of the Parkinson's disease kinase LRRK2", Nat Chem Biol. 2011: 7:203-205.
Dzamko, et al., "Inhibition of LRRK2 kinase activity leads to dephosphorylation on Ser910/Ser935, disruption of 14-3-3 binding and altered cytoplasmic localization", Biochem J. (2010): 430: 405-413.
Elbashir, et al., "Duplexes of 21-nucleotide RNAs mediate RNA interference in cultured mammalian cells", Nature, 411, 494-498, (2001).
Genbank "Mus musculus leucine-rich repeat kinase 2 (Lrrk2), mRNA", Accession No. NM_025730 (Mouse), (retrieved from the internet Nov. 27, 2017).
Genbank "*Homo sapiens* leucine rich repeat kinase 2 (LRRKS), mRNA", Accession No. NM_198578 (Human), (retrieved from the internet Nov. 27, 2017).
GenPept "leucine-rich repeat serine/threonine-protein kinase 2 [*Homo sapiens*]" Accession No. NP_940980 (Human), (retrieved from the internet Nov. 27, 2017).
Gloeckner, CJ., et al., "Phosphopeptide Analysis Reveals Two Discrete Clusters of Phosphorylation in the N-Terminus and the Roc Domain of the Parkinson-Disease Associated Protein Kinase LRRK2", J. Proteome Res. 2010: 9: 1738-1745.
Gruber, et al., "Efficient tumor cell lysis mediated by a bispecific single chain antibody expressed in *Escherichia coli*.", J. Immunol. 152:5368-5374, (1994).
Hampel, et al., "RNA Catalytic Properties of the Minimun (-)sTRSV Sequence", Biochemistry, 28:4929-4933, (1989).
Hampel, et al., "Hairpin' catalytic RNA model: evidence for helices and sequence requirement for substrate RNA", Nucleic Acids Research, 18: 299-304, (1990).
Haseloff, et al., "Simple RNA enzymes with new and highly specific endoribonuclease activities", Nature, 334:585-591 (1988).
Hollinger, et al., "'Diabodies": Small bivalent and bispecific antibody fragments", Proc. Natl. Acad. Sci. USA 90:6444-6448, (1993).
Huston, et al., "Protein engineering of antibody binding sites: Recovery of specific activity in an anti-digoxim single-chain Fv analogue produced in *Escherichia coli*", Proc. Nat. Acad. Sci. USA, 85:5879-5883, (1988).
Jang, et al., "Targeted degradation of proteins by PROTACs", Current Protocols Chem Biol, Jun. 1, 2010, 2(2): 71-87.
Kostelny, et al., "Formation of a bispecific antibody by the use of leucine zippers", J. Immunol. 148(5) 1547-1553, (1992).
Lee, et al., "Expression of small interfering RNAs targeted against HIV-1 rev transcripts in humas cells", Nature Biotechnol. 19:500-505, (2002).
Miyagishi, et al., "U6 promoter-driven siRNAs with four uridine 3' overhangs efficiently suppress targeted gene expression in mammalian cells", Nature Biotechtol. 19:497-500, (2002).
Nichols, et al, "Substrate specificity and inhibitors of LRRK2, a protein kinase mutated in Parkinson's disease", Biochem. J. (2009) 424, 47-60.
Nichols, et al., "A recombinase-based palindrome generator capable of producing randomized shRNA libraries", Journal of Biotechnology 143 (2009) 79-84.
Paddison, et al., "Short hairpin RNAs (shRNAs) induce sequence-specific silencing in mammalian cells", Genes & Devel. 16:948-958, (2002).
Paul, et al., "Effective expression of small interfering RNA in human cells", Nature Biotechnol. 20:505-508, (2002).
Power, et al., "Generation of recombinant multimeric antibody fragments for tumor diagnosis and therapy", Methods Mol Biol, 207, 335-50, 2003.
Rossi, et al., "Ribozymesas Anti-HIV-1 Therapeutic Agents: Principles, Applications, and Problems", Aids Research and Human Retroviruses, 8:183-190, 1992.
Schmajuk, et al., "Antisense Oligonucleotides with Different Backbones", The Journal of Biological Chemistry, vol. 274, No. 31, Issue of Jul. 30, pp. 21783-21789, 1999.
Stein, et al., 1993 Antisense oligonucleotides as therapeutic agents-1s the bullet really magical?, Science; Aug. 20, 1993; 261, 5124; p. 1004-1012.
Sui, et al., "A DNA vector-based RNAi technology to suppress gene expression in mammalian cells", Proc. Natl. Acad. Sci., USA, 99:5515-5520, (2002).
Tutt, et al., Trispecific f(ab'), derivatives that use cooperative signaling via the tcr/cd3 complex and cd2 to activate and redirect resting cytotoxic t cells, J. Immunol. 147:60-69, 1991.
Vermeire, et al., "Current status of genetics research in inflammatory bowel disese", Genes and Immunity 6, 637-645 (2005).
Wahl, et al., "Improved Radiology and Tumor Localization with Monoclonal F(ab')2", J. Nucl. Med. 24:316-325 (1983).
Wu, et al., "Anti-carcinoembryonic antigen (CEA) diabody for rapid tumor targeting and imaging", Tumor Targeting, 4, 47-58, 1999.
Yu, et al., "RNA interference by expression of short-interfering RNAs and hairpin RNAs in mammalian cells", Proc. Natl. Acad. Sci., USA, 99:6047-6052 (2002).
Zamore, et al., "RNAi: Double-Stranded RNA Directs the TP-Dependent Cleavage of mRNA at 21 to 23 Nucleotide Intervals", Cell, 101:25-33, 2000.
Zapata, et al., "Engineering linear F(ab')2 fragments for efficient production in *Escherichia coli* and enhanced antiproliferative activity", Protein Eng. 8(10): 1057-1062,1995.

* cited by examiner

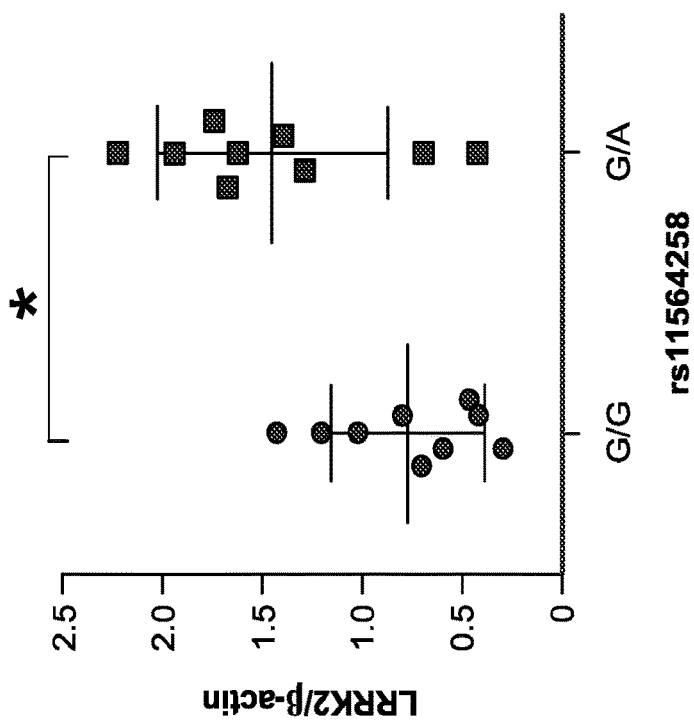
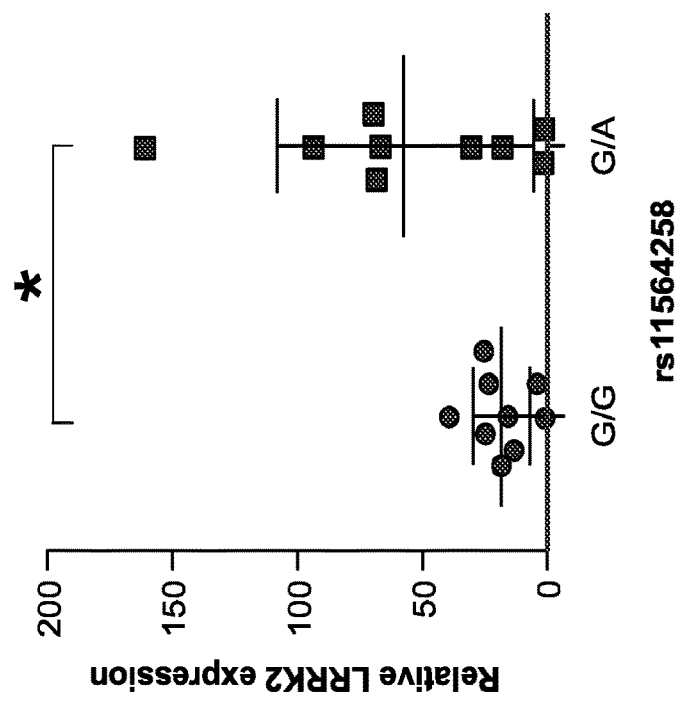
FIG. 1A
FIG. 1B

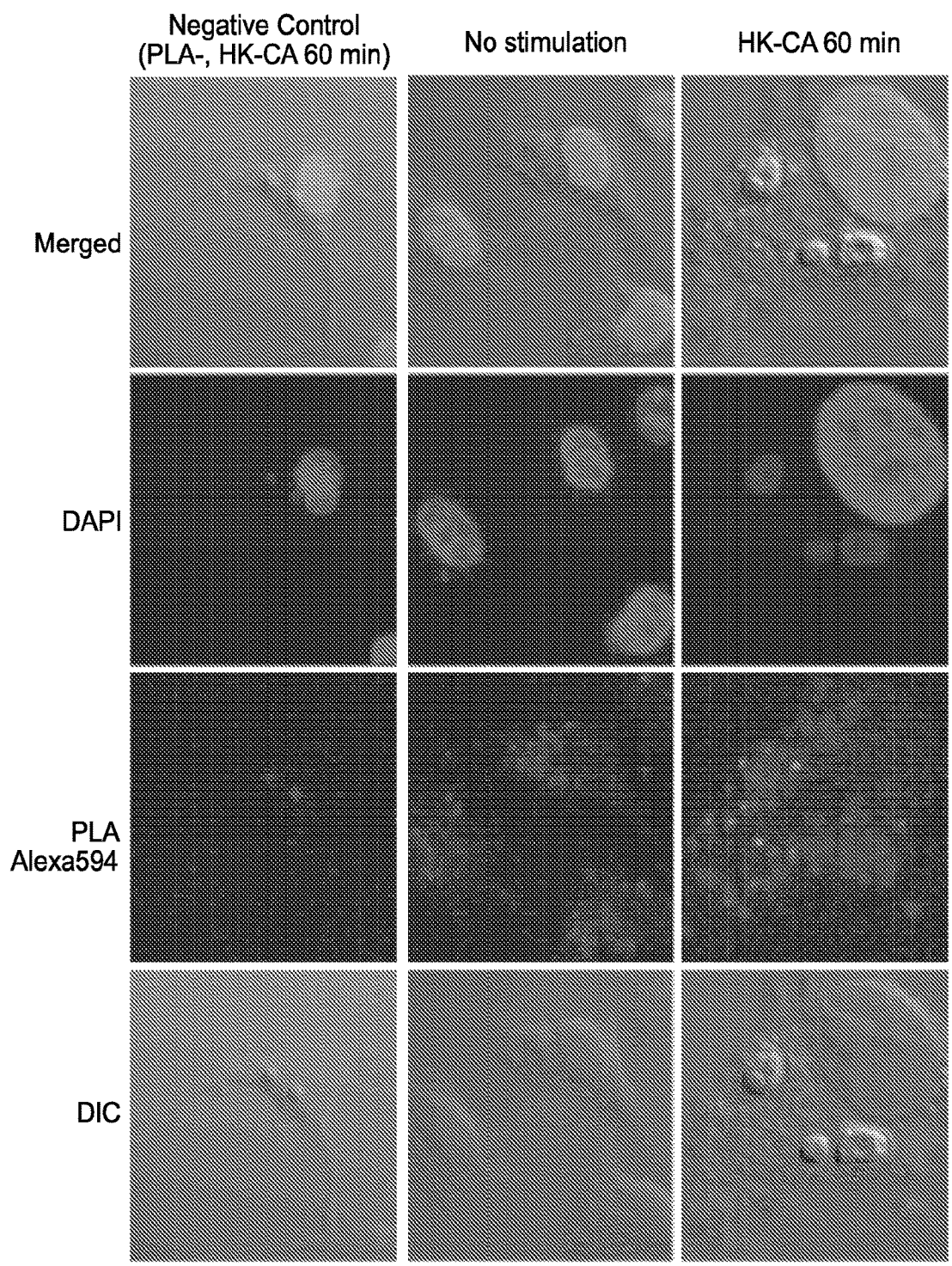

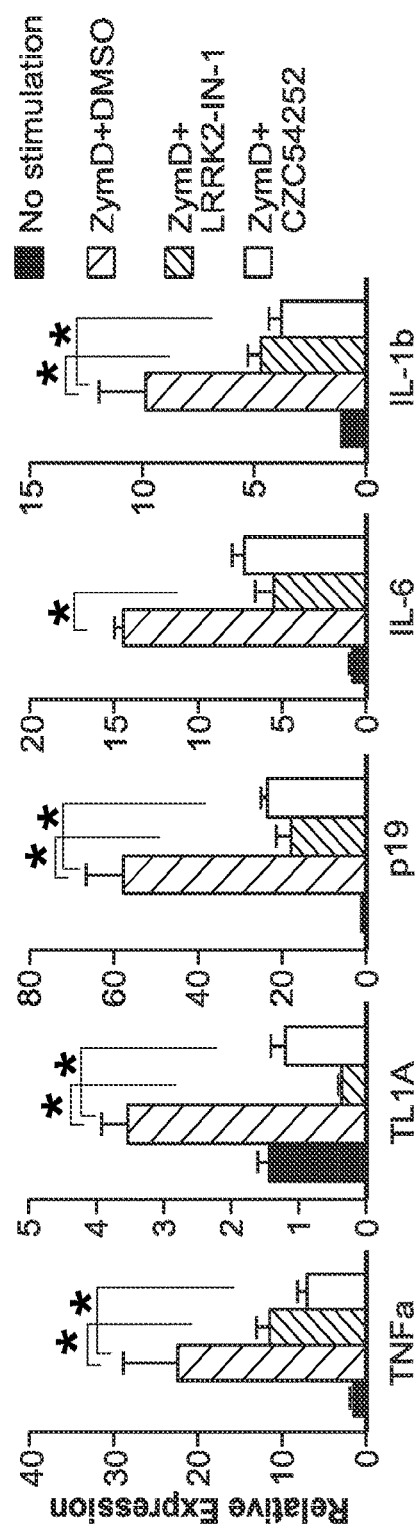
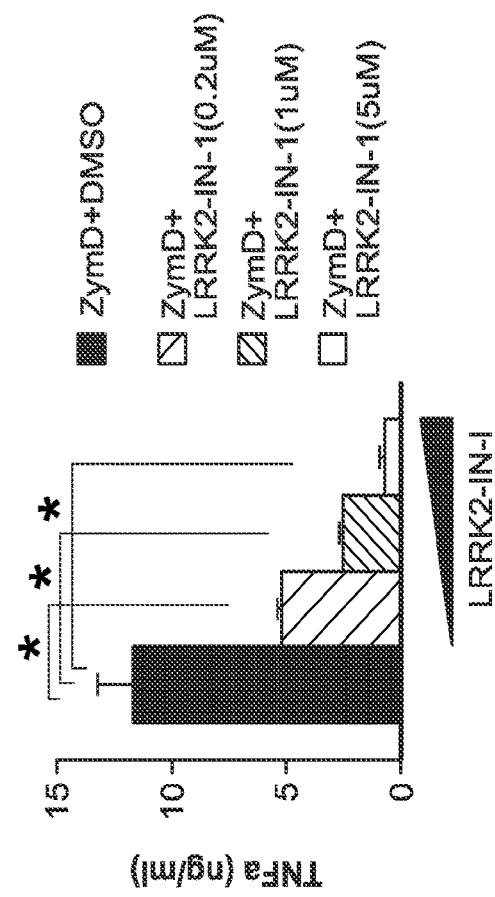
FIG. 5A
FIG. 5B

TREATMENT OR PREVENTION OF AN INTESTINAL DISEASE OR DISORDER

RELATED APPLICATIONS AND INCORPORATION BY REFERENCE

This application is a national stage entry of International Application No. PCT/US2015/031200 having an international filing date of May 15, 2014, which claims priority to U.S. Provisional Application Ser. No. 61/993,637, filed May 15, 2014, the entire contents of which are incorporated herein by reference in their entireties. All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

GOVERNMENT SUPPORT

This invention was funded by the National Institutes of Health. The United States Government has certain rights in this invention.

BACKGROUND OF THE INVENTION

Inflammatory Bowel Diseases (IBD) is a broad term that describes conditions with chronic or recurring immune response and inflammation of the gastrointestinal tract. Crohn's disease (CD) and ulcerative colitis (UC), the two common forms of idiopathic inflammatory bowel disease (IBD), are chronic, relapsing inflammatory disorders of the gastrointestinal tract. The peak age of onset for IBD is 15 to 30 years old, although it may occur at any age. About 10% of cases occur in individuals younger than 18 years. Ulcerative colitis is slightly more common in males, whereas Crohn's disease is marginally more frequent in women. IBD is one of the five most prevalent gastrointestinal disease burdens in the United States, with an overall health care cost of more than $1.7 billion. It is estimated that as many as 1.4 million persons in the United States suffer from these diseases.

The precise etiology of IBD remains to be elucidated. Genetic factors play an important role in IBD pathogenesis, as evidenced by the increased rates of IBD in Ashkenazi Jews, familial aggregation of IBD, and increased concordance for IBD in monozygotic compared to dizygotic twin pairs (Vermeire et al., Genes Immun 6, 637 (2005)). CD and UC are thought to be related disorders that share some genetic susceptibility loci but differ at others.

Thus, there remains a need in the art to develop methods to treat or prevent IBD, as well as to determine other genes or allelic variants that may assist in explaining the genetic risk, diagnosing, and/or predicting susceptibility or risk for inflammatory bowel disease including but not limited to CD and/or UC.

SUMMARY OF THE INVENTION

The present invention is based, at least in part, on the novel finding of leucine rich repeat kinase 2 (LRRK2) as an important intracellular pro-inflammatory component, and that an inhibitor of LRRK2 abrogates the pro-inflammatory activity of LRRK2 both in vitro and in vivo. Due to the newly-discovered impact of an inhibitor of LRRK2 in reduction of the pro-inflammatory activity of LRRK2, inhibitors of LRRK2 are therefore described herein for treatment of inflammatory diseases and disorders, e.g., CD and UC, as well as other inflammatory diseases and/or disorders.

In one aspect, the invention provides a method of treating or preventing an intestinal disease or disorder, the method involving administering to a subject a modulator of LRRK2 in an amount effective to treat or prevent the intestinal disease or disorder.

In one embodiment, the intestinal disease or disorder is an inflammatory bowel disease (IBD). In a related embodiment, the IBD is CD or UC.

In one embodiment, the LRRK2 modulator is an inhibitor. In certain embodiments, the LRRK2 modulator is a peptide or polypeptide, a small molecule or a nucleic acid inhibitor. In one embodiment, the polypeptide is an antibody, or fragment thereof. Optionally, the LRRK2 inhibitor is LRRK2-IN-1 or CZC54252.

In certain embodiments, the LRRK2 modulator is administered in combination with an additional agent. Optionally, the additional agent is an anti-inflammatory agent, an immunomodulator, an antibiotic or a non-steroidal anti-inflammatory drug.

Another aspect of the invention provides a method of determining the susceptibility or risk of a subject to develop an intestinal disease or disorder, the method involving obtaining a sample from the subject; assaying the sample to determine the expression of LRRK2; and determining the susceptibility or risk of the subject to develop an intestinal disease or disorder based on the expression of LRRK2.

A further aspect of the invention provides a method of diagnosing a subject with an intestinal disease or disorder, the method involving obtaining a sample from the subject; assaying the sample to determine the expression of LRRK2; and diagnosing a subject with an intestinal disease or disorder based on the expression of LRRK2.

In a preferred aspect, a subject is treated in accordance with the results of such methods for determining the susceptibility or risk to develop an intestinal disease or disorder, or methods to diagnosis an intestinal disease or disorder. For example, in a preferred aspect, methods for treating or preventing an intestinal disease or disorder are provided, the methods comprising:

obtaining a sample from a subject;
assaying the sample to determine the expression of LRRK2;
diagnosing a subject with an intestinal disease or disorder based on the expression of LRRK2,
administering to the subject diagnosed with an intestinal disease or disorder a modulator of LRRK2 in an amount effective to treat or prevent the intestinal disease or disorder.

In another preferred aspect, methods for treating or preventing an intestinal disease or disorder are provided, the methods comprising:

obtaining a sample from the subject;
assaying the sample to determine the expression of LRRK2;
determining the susceptibility or risk of the subject to develop an intestinal disease or disorder based on the expression of LRRK2; and
administering to the subject determined to be at risk to develop an intestinal disease or disorder a modulator of LRRK2 in an amount effective to treat or prevent the intestinal disease or disorder.

In one embodiment, the expression of LRRK2 increases with bowel inflammation. In another embodiment, the level of LRRK2 expression in a subject at a first point in time compared to a level of LRRK2 expression at a second point in time is used to determine the susceptibility of a patient to disease reoccurence.

In a further embodiment, the sample is whole blood, plasma, serum, saliva, cheek swab, urine or stool.

In another embodiment, the subject does not have intestinal inflammation.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DESCRIPTION OF THE DRAWINGS

FIG. 1a to FIG. 1e show the results of studies designed to evaluate how the SNP affected LRRK2 expression. LRRK2 mRNA and protein levels were compared in eight lymphoblastoid cell lines that were heterozygous for the risk allele (G/A) at rs11564258 with gender- and ethnicity-matched control cells lacking a risk allele (G/G) at this locus; studies were limited to heterozygous cells since the frequency of the risk allele (A) is very low and homozygous A/A cells were unavailable (a and b). LRRK2-Tg mice (as well as LRRK2 KO mice) were subjected to DSS (dextran-sulfate)-colitis. The transgenic mice did not display spontaneous colitis (in repeated studies) but did exhibit more severe DSS-colitis associated with enhanced pro-inflammatory cytokine secretion as compared with littermate control mice (FIGS. 1c-1e).

FIG. 4a to FIG. 4h show data relating to the effect of LRRK2 on autophagy. It was found with Western blot studies that BMDC from LRRK2-KO mice stimulated with irradiated *M. leprae* (*M leprae*) or ZymD exhibited increased LC3-II conversion, a marker of the induction of autophagy (FIG. 4a) whereas BMDC from LRRK2-Tg exhibited decreased LC3-II conversion (FIG. 4b) compared to control mice. This finding was then verified with studies of *M. leprae*- or ZymD-stimulated BMDCs from LRRK2 KO or LRRK2 Tg mice bearing an LC3-GFP gene that allowed the quantitation of the development of autophagy-associated LC3 puncta. It was found that LRRK2 KO cells exhibited increased numbers of LC3 puncta and cells from LRRK2 Tg exhibited decreased numbers of LC3 puncta (FIG. 4c and FIG. 4d). In related studies it was found that after stimulation with HK-CA, LRRK2 co-localizes with endosomal/lysosomal membrane marker, LAMP1 (FIG. 4e). Furthermore, using a Proximity Ligation Assay (in situ PLA) it was demonstrated that whereas in unstimulated BMDC uncomplexed LRRK2 is found in the cytosol or on vesicular membranes, in HK-CA-stimulated BMDC the LRRK2/Beclin-1 complex is found on an endosomal membrane (FIG. 4g). Finally, to determine if LRRK2 in association with TAB2 promotes Beclin-1 degradation, HEK293T cells were transfected with vectors expressing LRRK2, TAB2 and K48-ubiquitin alone or in combination and then analyzed by immunoblotting for Beclin-1 degradation bands and K48-polyubiquitination. It was found that LRRK2 transfection alone and in synergy with TAB2 transfection gave rise to Beclin-1 degradation bands and K48 polyubiquitination bands (FIG. 4h).

FIG. 5a to FIG. 5f show the results of studies performed to evaluate the effect of LRRK2 inhibitors on LRRK2 signaling leading to inflammation or autophagy. It was found that ZymD-induced cytokine production by BMDC from LRRK2 Tg mice was greatly reduced in the presence of two LRRK2 inhibitors, LRRK2-IN-1 and CZC54252 (FIG. 5a and FIG. 5b). In addition, human BMDC derived from Crohn's disease peripheral blood also exhibited suppressed ZymD-induced TNF-α production both at the transcriptional and protein levels in the presence of inhibitor. Furthermore, by Western blot and LC3 puncta studies it was found that the LRRK2 inhibitor, LRRK2-IN-1, reversed inhibition of autophagy in *M. leprae*- and ZymD-stimulated BMDC from LRRK2 Tg mice (FIG. 5c and FIG. 5d). Finally, administration of LRRK2 inhibitor LRRK-IN-1, to LRRK2-Tg mice leads to amelioration of DSS-colitis in such mice FIG. 5e and FIG. 5f).

DETAILED DESCRIPTION OF THE INVENTION

Figure 1D:
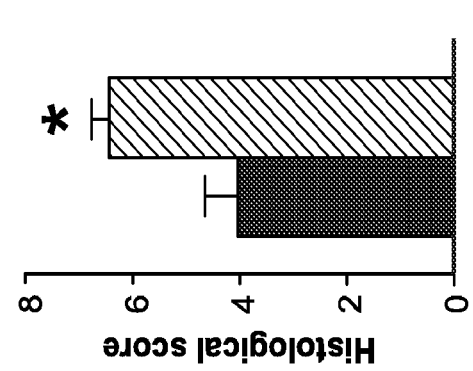
Figure 1C:
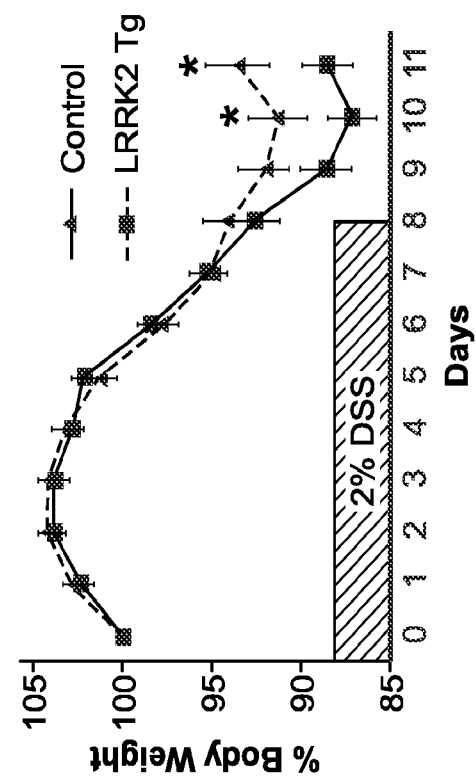
Figure 1E:
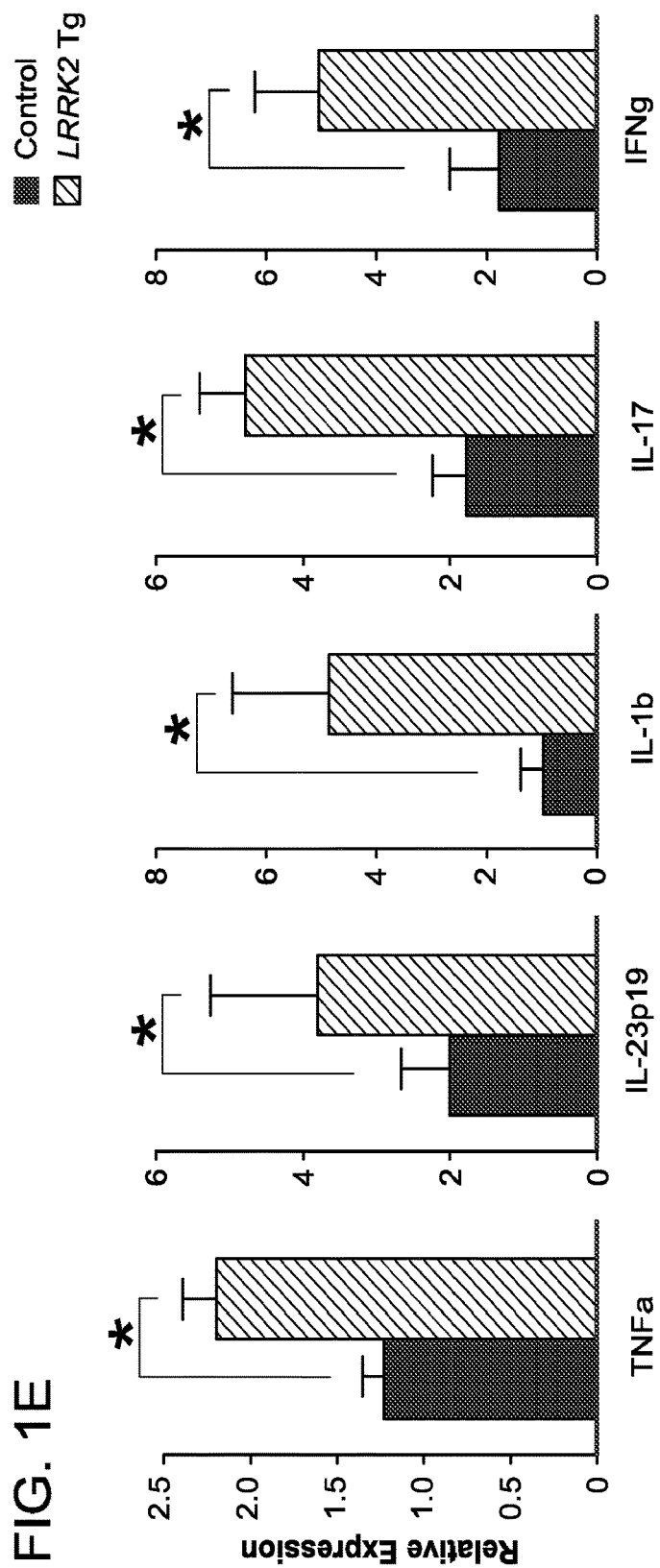

Described herein are novel methods and compositions for the treatment or prevention of intestinal diseases or disorders, and for determining the susceptibility or risk of intestinal diseases or disorders, based in part, on the present discovery of LRRK2 as an important intracellular pro-inflammatory factor in the pathogenesis of gut inflammation and that an inhibitor of LRRK2 abrogates that pro-inflammatory activity of LRRK2 both in vitro and in vivo.

Definitions

To facilitate an understanding of the present invention, a number of terms and phrases are defined below.

As used herein, the singular forms "a", "an", and "the" include plural forms unless the context clearly dictates otherwise. Thus, for example, reference to "a sensor" includes reference to more than one sensor.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, an "agent" is meant to refer to any substance that has an effect on treating or preventing an intestinal disease or disorder (e.g. CD or UC), or a condition associate with the intestinal disease or disorder. In certain embodiments, the agent is an anti-inflammatory agent, an immunomodulator, an antibiotic or a non-steroidal anti-inflammatory drug.

As used herein, the term "diagnosing" or "diagnose" refers to determining the nature or the identity of a condition or disease. A diagnosis may be accompanied by a determination as to the severity of the disease. Diagnosis as it relates to the present invention, relates to the diagnosis of an intestinal disease or disorder, preferably an idiopathic inflammatory bowel disease.

As used herein, the term "amount effective" or "effective amount" is meant to refer to that amount of the therapeutic agent (e.g., a modulator of LRRK2) that is sufficient to result in the treatment of an intestinal disease or disorder (e.g., CD or UC), to prevent advancement of an intestinal disease or disorder (e.g., CD or UC), or to enhance or improve the therapeutic effect(s) of another therapeutic agent administered to treat or prevent an intestinal disease or disorder (e.g., CD or UC).

As used herein, the term "intestinal disease or disorder" is meant to refer to a pathology of the gastrointestinal tract. In certain embodiments, the intestinal disease or disorder is an inflammatory bowel disease, preferably an idiopathic inflammatory bowel disease. By "inflammatory bowel disease" or "IBD" refers to gastrointestinal disorders including, but not limited to CD and UC. Inflammatory bowel diseases such as CD and UC are distinguished from all other disorders, syndromes, and abnormalities of the gastroenterological tract, including irritable bowel syndrome (IBS).

As used herein, "leucine rich repeat kinase 2 (LRRK2)" is meant to refer to a member of the leucine-rich repeat kinase family and encodes a protein with an ankryin repeat region, a leucine-rich repeat (LRR) domain, a kinase domain, a DFG-like motif, a RAS domain, a GTPase domain, a MLK-like domain, and a WD40 domain. The protein is present largely in the cytoplasm but also associates with the mitochondrial outer membrane. In certain embodiments, LRRK2 mRNA refers to GenBank Accession No. NM_198578 (human) or NM_025730 (mouse), and LRRK2 protein refers to GenBank Accession No. NP_940980 (human) or NP_080006 (mouse). A "modulator of leucine rich repeat kinase 2 (LRRK2)" as used herein is meant to refer to any substance that alters the activity or expression of LRRK2. The disclosure contemplates any modulator effect, including increased (e.g., activator agents) or decreased activity (e.g., inhibitor agents) and increased or decreased expression. Modulators and modulation may also include molecular strategies such as RNA interference (e.g., knockdown of protein synthesis at the mRNA level via siRNA molecules) or targeted protein degradation (e.g., ubiquitin-proteasome pathway in a targeted manner as described in Jong et al., "Targeted degradation of proteins by PROTACs" Current Protocols Chem Biol., 2010, Jun. 1; 2(2): 71-87, which is incorporated herein by reference).

In certain embodiments, the modulator of LRRK2 is an inhibitor of LRRK2.

As used herein, the term "risk allele" is meant to refer to genetic variants, the presence of which correlates with an increase or decrease in susceptibility to an intestinal disorder, preferably an inflammatory bowel disorder (IBD). Risk alleles include, but are not limited to variants at the LRRK2/MUC19 genetic locus, such as "haplotypes" and/or a set of single nucleotide polymorphisms (SNPs) on a gene or chromatid that are statistically associated. More preferably, risk alleles can include, but are not limited to rs11564258.

As used herein, the term "sample" is meant to refer to any biological material obtained from an individual. Examples of a biological sample include, but are not limited to whole blood, plasma, serum, saliva, cheek swab, urine, stool, or other bodily fluid or tissue that contains nucleic acid.

As used herein, the term "subject" is meant to refer to an animal, preferably a mammal including a non-primate (e.g., a cow, pig, horse, cat, dog, rat, and mouse) and a primate (e.g., a monkey, such as a cynomolgus monkey, and a human), and more preferably a human. In a preferred embodiment, the subject is a human.

As used herein, the term "susceptibility" refers to predicting the probable course and outcome of an intestinal disease or disorder (e.g. CD or UC) or the likelihood of recovery from an intestinal disease or disorder (e.g. CD or UC). Determining the susceptibility can include the presence, the outcome, or the aggressiveness of the disease.

As used herein, the term "treating" is meant to refer to both therapeutic treatment and prophylactic or preventative measures, wherein the object is to prevent, slow down and/or lessen the disease even if the treatment is ultimately unsuccessful. Those in need of treatment include those already with an intestinal disease or disorder (e.g. CD or UC), as well those prone to have an intestinal disease or disorder (e.g. CD or UC) or those in whom an intestinal disease or disorder (e.g. CD or UC) is to be prevented. For example, in treatment or the intestinal disease or disorder, a therapeutic agent may directly decrease the pathology of an inflammatory bowel disease (e.g. CD or UC), or render the cells of the gastroenterological tract more susceptible to treatment by other therapeutic agents.

Unless specifically stated or obvious from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, apparatus, or methods provided herein can be combined with one or more of any of the other compounds, compositions, apparatus, and methods provided herein.

Intestinal Diseases or Disorders

In certain embodiments, a LRRK2 modulator (e.g., a LRRK2 inhibitor), is used to treat intestinal diseases or disorders, such as idiopathic inflammatory bowel disease, which includes two syndromes, CD and UC. A LRRK2 modulator of the invention also can be administered with one or more additional therapeutic agents useful in the treatment of intestinal disorders, as discussed further herein.

Crohn's Disease (CD)

CD is an inflammatory bowel disease (IBD). It causes inflammation of the lining of the digestive tract, which can lead to abdominal pain, severe diarrhea and malnutrition. Inflammation caused by CD can involve different areas of the digestive tract in different people. The variable clinical manifestations of CD are, in part, a result of the varying anatomic localization of the disease. The most frequent symptoms of CD are abdominal pain, diarrhea and recurrent fever. However, CD is also commonly associated with intestinal obstruction or fistula, the latter consisting of an abnormal passage between diseased loops of bowel or between the latter and other organs. CD also includes complications such as inflammation of the eye, joints and skin; liver disease; kidney stones or amyloidosis. In addition, CD is associated with an increased risk of intestinal cancer Several features are characteristic of the pathology of CD. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display the typical discrete granulomas, while others show a diffuse granulomatous reaction or nonspecific transmural inflammation. As a result, the presence of discrete granulomas is indicative of CD, although the absence of granulomas also is consistent with the disease. Thus, transmural or discontinuous inflammation, rather than the presence of granulomas, is a preferred diagnostic indicator of CD (Rubin and Farber, Pathology (Second Edition) Philadelphia: J.B. Lippincott Company (1994)).

Ulcerative Colitis(UC)

UC is a chronic disease of the large intestine, also known as the colon, in which the lining of the colon becomes inflamed and develops tiny open sores, or ulcers, that produce pus and mucous. The combination of inflammation and ulceration can cause abdominal discomfort and frequent emptying of the colon (diarrhea).

CD can affect any part of the gastrointestinal (GI) Tract, but UC affects only the colon. Additionally, while CD can affect all layers of the bowel wall, ulcerative colitis only affects the lining of the colon.

Characteristics that serve to distinguish Crohn's disease from ulcerative colitis are summarized in Table 1, below (Rubin and Farber (1994), supra).

TABLE 1

Characteristic Features of Crohn's disease and ulcerative colitis

| Feature | Crohn's Disease | Ulcerative Colitis |
|---|---|---|
| Macroscopic | | |
| Thickened bowel wall | Typical | Uncommon |
| Luminal narrowing | Typical | Uncommon |
| "Skip" lesions | Common | Absent |

TABLE 1-continued

Characteristic Features of Crohn's disease and ulcerative colitis

| Feature | Crohn's Disease | Ulcerative Colitis |
|---|---|---|
| Right colon predominance | Typical | Absent |
| Fissures and fistulas | Common | Absent |
| Circumscribed ulcers | Common | Absent |
| Confluent linear ulcers | Common | Absent |
| Pseudopolyps | Absent | Common |
| Microscopic | | |
| Transmural inflammation | Typical | Uncommon |
| Submucosal fibrosis | Typical | Absent |
| Fissures | Typical | Rare |
| Granulomas | Common | Absent |
| Crypt abscesses | Uncommon | Typical |

Causes of Inflammatory Bowel Disease

There is now a general consensus that both forms of inflammatory bowel disease described above are caused by an abnormal immune response to the microbiota present in the small and large intestine, i.e., intestinal microbiome. The cause of this abnormal response is multifactorial. In some cases, it can be due to abnormalities of the normal constraints on mucosal response to constituents of the microbiome. However, it can also be due to excessive immune responses of immune cells due to abnormalities intrinsic to such cells. This latter type of abnormality is likely to be the cause of IBD in patients with genetic abnormalities involving LRRK2. In this case, the abnormal LRRK2 mediates excessive immune responses by dendritic cells in the mucosa upon encounter of the latter with the normal microbiome. On this basis, agents that inhibit LRRK2 are likely suppress the abnormal immune response and ameliorate disease.

LRRK2 Modulators

The present invention contemplates, generally, administering to a subject a modulator of leucine rich repeat kinase 2 (LRRK2). Potential modulators of a LRRK2 polypeptide include organic molecules, peptides, peptide mimetics, polypeptides, nucleic acid molecules (e.g., double-stranded RNAs, siRNAs, antisense polynucleotides), and antibodies that bind to a LRRK2 nucleic acid sequence or polypeptide of the invention and thereby inhibit or extinguish its activity.

In certain preferred embodiments, the LRRK2 modulators are LRRK2 inhibitors. Preferably, the LRRK2 inhibitors are small molecule inhibitors.

Small Molecule Inhibitors

By small molecule inhibitor is meant to refer to a small molecule that is a low molecular weight (i.e. <900 Daltons) organic compound. The present disclosure contemplates use of the following small molecule LRRK2 inhibitors in the methods and compositions described herein (but is not limited to such molecules):

GSK2578215A (5-(2-Fluoro-4-pyridinyl)-2-(phenylmethoxy)-N-3-pyridinylbenzamide; Tocris Biosciences, product no. 4629) is a small molecule LRRK2 inhibitor. $IC_{50}$ values are 8.9 and 10.1 nM for LRRK4[G2019S] mutant and wild-type LRRK2 respectively. GSK2578215 displays selectivity for LRRK2 against a panel of 460 other kinases. It blocks Ser910 and Ser935 phosphorylation in vitro and in peripheral tissues in vivo, and is brain penetrant. The chemical structure of GSK2578215 is shown below.

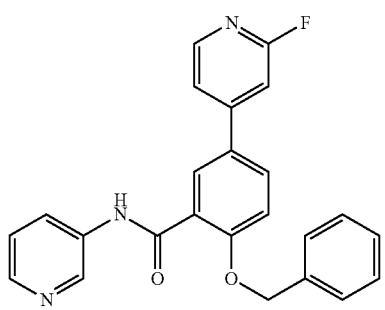 [SMILES: O=C(Nc1cccnc1)c1cc(-c2ccnc(F)c2)ccc1OCc1ccccc1]

HG-10-102-01 (Leucine-Rich Repeat Kinase 2 Inhibitor III, Mixed-Lineage Kinase 1 Inhibitor I, MLK1 Inhibitor I, MNK Inhibitor III, (4-(5-Chloro-4-(methylamino)pyrimidin-2-ylamino)-3-methoxyphenyl)(morpholino)methanone; EMD Millipore, product no. 438195) is a cell-permeable 2,4-diaminopyrimidinyl compound that acts as a potent, ATP-competitive LRRK2-selective inhibitor and has $IC_{50}$ values=20.3, 3.2, 153.7 and 95.9 nM, respectively, against normal human LRRK2 and G2019S, A2016T, G2019S/A2016T LRRK2 mutants; [ATP]=100 μM), also displaying much reduced potency against MNK2 and MLK1 ($IC_{50}$=0.6 and 2.1 μM, respectively; [ATP]=100 μM) and little activity toward a panel of 136 other kinases. HG-10-102-01 is effective against cellular A2016T and G2019S/A2016T LRRK2 phosphorylations (IC50<3 μM). HG-10-102-01 can cross the blood-brain-barrier for LRRK2 phosphorylation inhibition in mice (30 mg/kg to 50 mg/kg i.p.) in vivo.

The chemical structure of HG-10-102-01 is shown below.

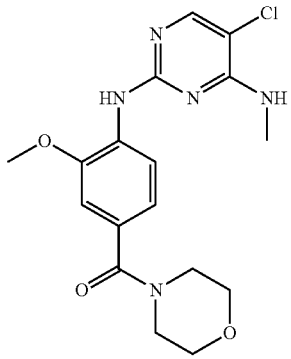

GNE-7915 ((4-((4-(ethylamino)-5-(trifluoromethyl)pyrimidin-2-yl)amino)-2-fluoro-5-methoxyphenyl)(morpholino)methanone; MedKoo biosciences, product no. 510257) was reported as a potent ($IC_{50}$=9 nM) selective (1/187 kinases), brain-penetrant and non-toxic inhibitor of LRRK2. The chemical structure of GNE-7915 is shown below.

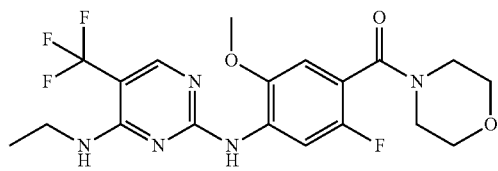 [SMILES: CCNc1nc(Nc2cc(F)c(C(=O)N3CCOCC3)cc2OC)ncc1C(F)(F)F]

CZC-25146 (N-(2-(5-Fluoro-2-(2-methoxy-4-morpholinophenylamino)pyrimidin-4-ylamino)phenyl)methanesulfonamide, HCl, N-(2-(2-(2-Methoxy-4-morpholinophenylamino)-5-fluoropyrimidin-4-ylamino)phenyl)methanesulfonamide, HCl; EMD Millipore, product no. 438194) is an orally bioavailable fluoro-diaminopyrimidine compound that acts as a potent, reversible and ATP-competitive inhibitor of LRRK2 activity ($IC_{50}$=4.76 and 6.87 nM for hr-wt-LRRK2 and G2019S-LRRK2 mutant, respectively) with selectivity over PLK4, GAK, TNK1, CAMKK2, and PIP4K2C (IC50<300 nM) in a 185-kinase panel. The chemical structure of CZC-25146 is shown below.

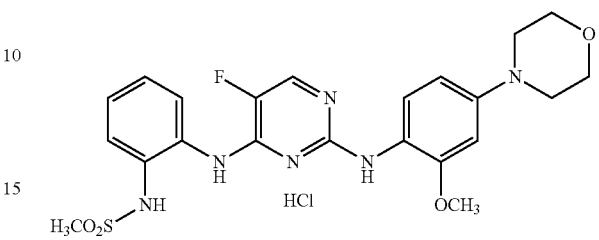

In certain embodiments, the small molecule LRRK2 inhibitor is LRRK2-In-1(5,11-Dihydro-2-[[2-methoxy-4-[[4-(4-methyl-1-piperazinyl)-1-piperidinyl]carbonyl]phenyl]amino]-5,11-dimethyl-6H-pyrimido[4,5-b][1,4]benzodiazepin-6-one; Tocris Bioscience, product no. 4273). LRRK2-In-1 inhibits both G2019S mutant and wild-type LRRK2 kinase activity ($IC_{50}$ values are 6 and 13 nM respectively). The chemical structure of LRRK2-In-1 is shown below.

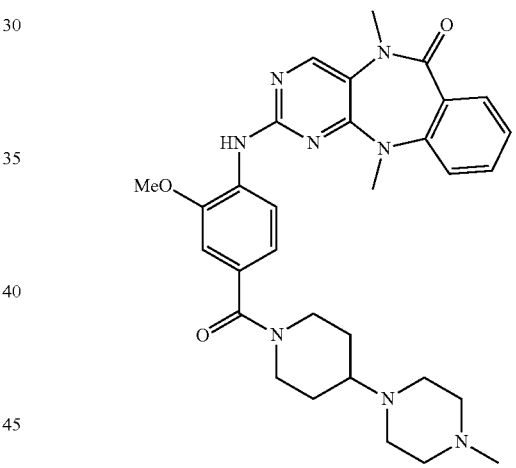

In other embodiments, the small molecule LRRK2 inhibitor is CZC-54252 hydrochloride (N-[-[[5-Chloro-2-[[2-methoxy-4-(4-morpholinyl)phenyl]amino]-4-pyrimidinyl]amino]phenyl]methanesulfonamide hydrochloride; R&D systems, product no. 4534). The chemical structure of CZC-54252 is shown below.

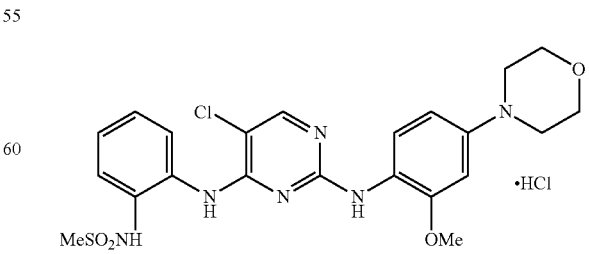

Other small molecule inhibitors previously reported to have inhibitory activities of LRRK2 kinase include, but are not limited to, TAE684, Indirubin-3-monoxime, Sunitinib, GW5074, H-89. Further, several ROCK (Rho kinase) inhibitors such as H-89, fasudil (HA-1077), hydroxyfasuldil (HA-1100), H-1152, Y-27632, GSK429286A, GSK269962A and sunitinib have been shown to suppress LRRK2 with similar potency to which they inhibited ROCK2 (Nichols et al., Biochem. J. (2009) 424, 47-60, incorporated by reference in its entirety herein).

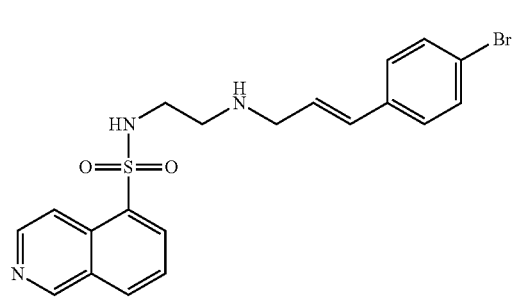

H-89

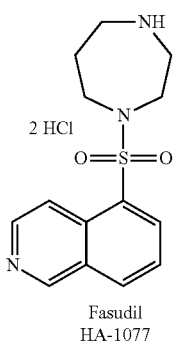

Fasudil
HA-1077

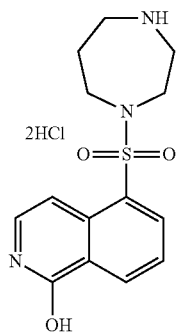

Hydroxyfasudil
HA-1100

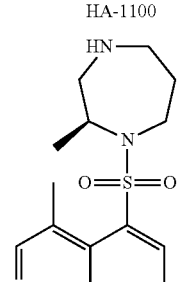

H-1152

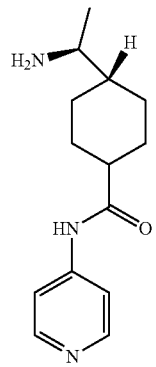

Y-27632

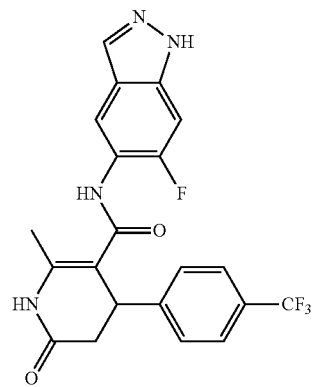

GSK429286A

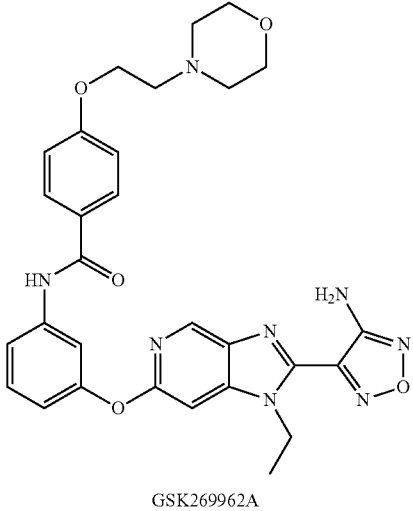

GSK269962A

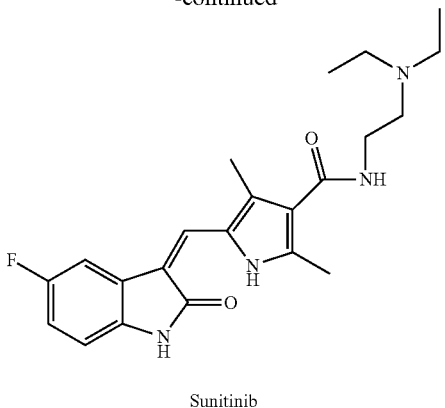

Sunitinib

While the above specific compounds are examples of LRRK2 inhibitors contemplated herein, the methods and compositions disclosed here contemplate any suitable LRRK2 previously disclosed in the art or those not yet discovered. The following U.S. patent documents disclose an array of LRRK2 inhibitors, all of which are incorporated herein by reference: U.S. Pat. No. 8,815,882 (Pyrazole aminopyrimidine derivatives as LRRK2 modulators); U.S. Pat. No. 8,809,331 (Aminopyrimidine derivatives as LRRK2 modulators); U.S. Pat. No. 8,802,674 (Aminopyrimidine derivatives as LRRK2 modulators); U.S. Pat. No. 8,796,296 (Aminopyrimidine derivatives as LRRK2 modulators); U.S. Pat. No. 8,791,130 (Aminopyrimidine derivatives as LRRK2 modulators); U.S. Pat. No. 8,778,939 (Compounds); U.S. Pat. No. 8,409,809 (KASPP (LRRK2) gene, its production and use for the detection and treatment of neurodegenerative disorders); U.S. Pat. No. 8,354,420 (Aminopyrimidine derivatives as LRRK2 inhibitors); U.S. Pat. No. 8,206,942 (Methods of identifying LRRK2 inhibitors); U.S. Pat. No. 8,029,986 (KASPP (LRRK2) gene, its production and use for the detection and treatment of neurodegenerative disorders; and U.S. Pat. No. 7,947,468 (Methods).

Peptide or Polypeptide Inhibitors

Peptide or polypeptide inhibitors may be antibodies, for example antibodies that inhibit the kinase activity of LRRK2. Several of the LRRK2 domains are phosphorylated through both autophosphorylation and constitutive phosphorylation (Gloeckner C J, et al. J Proteome Res. 2010; 9:1738-1745). In particular, phosphorylation of serine 935 (pS935) has been linked to kinase activity in LRRK2 (Dzamko N et al. Biochem J. 2010; 430:405-413), where LRRK2 kinase inhibition has been shown to decrease pS935 in HEK 293 cells (Deng X et al. Nat Chem Biol. 2011; 7:203-205).

Antibodies useful in the invention include any antibody capable of selectively inhibiting LRRK2, for example an antibody that inhibits LRRK2 kinase activity. A polypeptide that "selectively binds" LRRK2 is one that binds a LRRK2 receptor, but that does not substantially bind other molecules in a sample, for example, a biological sample. Preferably, such an antibody binds with an affinity constant less than or equal to 10 mM.

Antibodies that selectively inhibit LRRK2 are useful in the methods of the invention. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non specific tissue binding of an intact antibody (Wahl et al., J. Nucl. Med. 24:316 325 (1983). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cells of interest. These multimeric scFvs (e.g., diabodies, tetrabodies) offer an improvement over the parent antibody since small molecules of ~60-100 kDa in size provide faster blood clearance and rapid tissue uptake. See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (scFv) dimers is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including VH- and VL-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

An antibody may be a monoclonal antibody. Alternatively, the antibody may be a polyclonal antibody. The preparation and use of polyclonal antibodies are also known to the skilled artisan. The invention also encompasses hybrid antibodies, in which one pair of heavy and light chains is obtained from a first antibody, while the other pair of heavy and light chains is obtained from a different second antibody. Such hybrids may also be formed using "chimeric" antibodies composed of humanized heavy and light chains.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated a "F(ab)2" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing LRRK2 or a LRRK2 receptor, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface Immunization of a suitable host can be carried out in a number of ways known in the art.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

LRRK2 antibodies are commercially available from a number of sources, including Santa Cruz Biotechnology (product nos. 48733, 66954, 130159), Cell Signalling Technology (product no. 5559) and Epitomics (product no. 3514, 3515, 3516, 5097, 5098, 5099). Davies et al. (Biochem Journal (2013) Jul. 1 453(1): 101-113) report optimized protocols and results for ten monoclonal antibodies for immunoblotting, immunohistochemistry, immunoprecipitation and kinase assays in rat, mouse and human brain tissue.

LRRK2 antibodies may also be used in techniques to measure LRRK2 expression, for example in a clinical setting prior to and after treatment.

Nucleic Acid Inhibitors

In certain embodiments, the LRRK2 modulator may be a LRRK2 inhibitory nucleic acid. An "inhibitory nucleic acid" is meant to refer to a single or double-stranded RNA, siRNA (short interfering RNA), shRNA (short hairpin RNA), or antisense RNA, or a portion thereof, or a mimetic thereof, that when administered to a cell results in a decrease (e.g., by 10%, 25%, 50%, 75%, or even 90-100%) in the expression of a target gene. Typically, a nucleic acid inhibitor comprises or corresponds to at least a portion of a target nucleic acid molecule, or an ortholog thereof, or comprises at least a portion of the complementary strand of a target nucleic acid molecule.

LRRK2 inhibitory nucleic acid molecules are essentially nucleobase oligomers that may be employed as single-stranded or double-stranded nucleic acid molecule to decrease LRRK2 expression. In one approach, the LRRK2 inhibitory nucleic acid molecule is a double-stranded RNA used for RNA interference (RNAi)-mediated knock-down of LRRK2 gene expression. In one embodiment, a double-stranded RNA (dsRNA) molecule is made that includes between eight and twenty-five (e.g., 8, 10, 12, 15, 16, 17, 18, 19, 20, 21, 22, 23, 24, 25) consecutive nucleobases of a nucleobase oligomer of the invention. The dsRNA can be two complementary strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. Double stranded RNA can be made using standard techniques (e.g., chemical synthesis or in vitro transcription). Kits to accomplish this are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference. An inhibitory nucleic acid molecule that "corresponds" to an LRRK2 gene comprises at least a fragment of the double-stranded gene, such that each strand of the double-stranded inhibitory nucleic acid molecule is capable of binding to the complementary strand of the target LRRK2 gene. The inhibitory nucleic acid molecule need not have perfect correspondence to the reference LRRK2 sequence. In one embodiment, an siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleobase sequence of the inhibitory nucleic acid molecule exhibits 1, 2, 3, 4, 5 or more mismatches.

"siRNA" refers to small interfering RNA; a siRNA is a double stranded RNA that corresponds to or matches a reference or target gene sequence. This matching need not be perfect so long as each strand of the siRNA is capable of binding to at least a portion of the target sequence. siRNA can be used to inhibit gene expression, see for example Bass, 2001, Nature, 411, 428 429; Elbashir et al., 2001, Nature, 411, 494 498; and Zamore et al., Cell 101:25-33 (2000). LRRK2 siRNAs are commercially available, for example from Santa Cruz Biotechnology (product no. sc-45380).

The inhibitory nucleic acid molecules provided by the invention are not limited to siRNAs, but include any nucleic acid molecule sufficient to decrease the expression of a LRRK2 nucleic acid molecule or polypeptide. For example, shRNA (short hairpin RNA) methods have also been described to reduce LRRK2 expression (Nichols et al. (2009)).

An "antisense nucleic acid", it is meant to refer to a non-enzymatic nucleic acid molecule that binds to target RNA by means of RNA--RNA or RNA-DNA interactions and alters the activity of the target RNA (for a review, see Stein et al. 1993; Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk N A et al., 1999; Delihas N et al., 1997; Aboul-Fadl T, 2005.)

Each of the DNA sequences provided herein may be used, for example, in the discovery and development of therapeutic antisense nucleic acid molecule to decrease the expression of LRRK2. The invention further provides catalytic RNA molecules or ribozymes. Such catalytic RNA molecules can be used to inhibit expression of a LRRK2 nucleic acid molecule in vivo. The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591 (1988), and U.S. Patent Application Publication No. 2003/0003469 A1, each of which is incorporated by reference. In various embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In one embodiment, the inhibitory nucleic acid molecules of the invention are administered systemically in dosages between about 1 and 100 mg/kg (e.g., 1, 5, 10, 20, 25, 50, 75, and 100 mg/kg).

Other Therapeutic Agents

In certain embodiments, the LRRK2 modulator is administered in combination with an additional agent. The language "in combination with" a therapeutic agent includes co-administration of a LRRK2 modulator of the invention with a therapeutic agent, administration of a LRRK2 modulator first, followed by the therapeutic agent and administration of the therapeutic agent first, followed by the LRRK2 modulator of the invention. Specific therapeutic agents are generally selected based on the particular disorder being treated, as discussed below.

Non-limiting examples of therapeutic agents for intestinal disorders, such as idiopathic inflammatory bowel disease, including Crohn's disease and ulcerative colitis, with which a LRRK2 modulator of the invention can be combined include, but are not limited to, the following: anti-inflammatory agents (e.g. sulfasalazine, mesalamine, corticosteroids); immunomodulators (e.g. azathioprine, mercaptopurine, infliximab, adalimumab, certolizumab pegol, methotrexate, cyclosporine, atalizumab) antibiotics (e.g. metronidazole, ampicillin, ciprofloxacin); non-steroidal anti-inflammatory drugs (NSAIDs).

The additional or second therapeutic agent can also include agents for treating disorders other than IBD. For example, the second therapeutic agent can be selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, antiinfectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

When the second therapeutic agent is a chemotherapeutic agent, the chemotherapeutic agent can be selected from, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; pipo-sulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

The second or additional therapeutic agent can also be an anti-angiogenic agent, such as, for example, angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline.

Methods

The present invention features methods of treating or preventing an intestinal disease or disorder comprising administering to a subject a modulator of leucine rich repeat kinase 2 (LRRK2) in an amount effective to treat or prevent an intestinal disease or disorder.

Preferably, the intestinal disease or disorder is an inflammatory bowel disease, more preferably Crohn's disease and ulcerative colitis.

Modulators of LRRK2 have been discussed in detail above. In certain embodiments, the LRRK2 modulator is an inhibitor, for example peptides or polypeptides, small molecules and nucleic acid inhibitors. It is contemplated in certain embodiments that the LRRK2 inhibitor is administered in combination with an additional therapeutic agent, which may include therapeutic agents for treating IBD, or may include therapeutic agent for treating other disorders which are not IBD.

Aspects of the present invention also feature methods of determining the susceptibility or risk of a subject to develop an intestinal disease or disorder comprising obtaining a sample from the subject, assaying the sample to determine the expression of LRRK2, and determining the susceptibility or risk of a subject to develop an intestinal disease or disorder based on the expression of LRRK2.

The invention also features methods of diagnosing a subject with an intestinal disease or disorder comprising obtaining a sample from the subject assaying the sample to determine the expression of LRRK2; and diagnosing a subject with an intestinal disease or disorder based on the expression of LRRK2.

Preferably, the intestinal disease or disorder is an inflammatory bowel disease, more preferably Crohn's disease or ulcerative colitis.

In certain embodiments of the methods described herein, assaying the sample comprises determining LRRK2 expression. Methods of determining protein expression include, but are not limited to immunoprecipitation, immunoelectrophoresis, Western blot, BCA assay (to quantify protein concentrations), spectrophotometry or enzyme assays such as enzyme-linked immunosorbent assay (ELISA).

In certain embodiments, the expression of LRRK2 increases with bowel inflammation.

In certain embodiments of the present invention, the level of expression of LRRK2 is determined, and then compared to a threshold level to determine if the subject is a candidate for treatment with a LRRK2 inhibitor.

A sample useful in the methods of the invention can be obtained from any biological fluid having antibodies such as, for example, whole blood, plasma, saliva, or other bodily fluid or tissue, preferably serum. In one embodiment, a method of the invention is practiced with whole blood, which can be obtained readily by relatively non-invasive means. In another embodiment, a method of the invention is practiced with tissue obtained from an individual such as tissue obtained during surgery or biopsy procedures.

It is to be understood that in practicing the methods of the invention, the subject may not have intestinal inflammation. That is, LRRK2 levels may not be increased or decreased.

Accordingly, in particular embodiments, the methods of the invention are useful for determining if a patient is in remission, or if a patient has a family history of inflammatory bowel disease. For example, the invention features methods of diagnosing a subject with an intestinal disease or disorder comprising obtaining a sample from the subject; assaying the sample to determine the expression of LRRK2; and diagnosing a subject with an intestinal disease or disorder based on the expression of LRRK2, where the expression of LRRK2 increases with bowel inflammation.

In further embodiments, the level of LRRK2 expression in a subject at a first point in time is compared to a level of LRRK2 expression at a second point in time, and is used to determine the susceptibility of a patient to disease reoccurrence.

Accordingly, a subpopulation of subjects can be identified where LRRK2 levels are elevated.

Patient Monitoring

The disease state or treatment of a patient having an intestinal disease or disorder (e.g. CD or UC) can be monitored using the methods of the invention. Such monitoring may be useful, for example, in assessing the efficacy of a particular drug in a patient and for monitoring the progression of the intestinal disease or disorder.

For example, in certain aspects the activity and/or expression level of LRRK2 is increased in proportion to the level of IBD. Thus, the activity and/or expression level of LRRK2 may be measured or tracked before, during, and/or after the administration of an anti-IBD treatment, such as treatment with an LRRK2 modulator or when combined with another anti-IBD treatment, such as anti-inflammatory agents (e.g. sulfasalazine, mesalamine, corticosteroids); immunomodulators (e.g. azathioprine, mercaptopurine, infliximab, adalimumab, certolizumab pegol, methotrexate, cyclosporine, atalizumab) antibiotics (e.g. metronidazole, ampicillin, ciprofloxacin); non-steroidal anti-inflammatory drugs (NSAIDs). Measurement of LRRK2 activity and/or expression may be achieved using the herein described methods, which include, but are not limited to, antibody-based detection (e.g., Western blotting using LRRK2 antibodies, PCR detection using LRRK2-specific nucleic acid probes/primers, and/or nucleic acid hybridization techniques using LRRK2-specific hybridization probes (e.g., Southern blotting).

Such detection techniques for detecting and/or quantitatively measuring specific proteins and/or genes and/or nucleic acid molecules of interest are well known in the art and are explained fully in the literature, such as, "Molecular Cloning: A Laboratory Manual", second edition (Sambrook, Cold Spring Harbor Laboratory Press, New York.); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel et al., Wiley Interscience, New York, 2001)); "PCR: The Polymerase Chain Reaction", (Mullis, 1994); "Current Protocols in Immunology" (Coligan, 1991). These techniques are applicable to the detection and/or quantitative measurement of the polynucleotides and polypeptides of the invention, and, as such, may be considered in making and practicing the invention.

Formulation, Administration, and Dosage of Pharmaceutical Compositions

The administration of a compound for the treatment of an intestinal disease or disorder may be by any suitable means that results in a concentration of the therapeutic that, combined with other components, is effective in ameliorating, reducing, or stabilizing IBD. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In one aspect, the compositions or agents disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Other preferred administration forms include for example oral administration forms such as tablets, capsules and others, intranasal, and patches or other transdermal administration. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin.

The amount of the therapeutic agent to be administered varies depending upon the manner of administration, the age and body weight of the patient, and with the clinical symptoms of the IBD, as well as other factors that will be generally known in the art. Generally, amounts will be in the range of those used for other agents used in the treatment of other diseases associated with IBD, although in certain instances lower amounts will be needed because of the increased specificity of the compound.

In other embodiments, human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

For mice in vivo experiments, a dosage of 10 mg/kg of LRRK2-IN-1 can be used. Dosages in human cells can be higher. For example, 5 uM would be required in order to suppress cytokine production. If the inhibitor is used for human in vivo study, more than 10 mg/kg, probably between 10-100 mg/kg, preferably 20-80 mg/kg, and most preferably 30-50 mg/kg, for example 30, 31, 32, 33, 34, 35, 36, 37, 38, 39, 40, 41, 42, 43, 44, 45, 46, 47, 48, 49 and 50 mg/kg can be an effective dose.

In certain embodiments, an LRRK2 modulator can be administered to the subject using a pharmaceutically-acceptable formulation. In certain embodiments, these pharmaceutical compositions are suitable for oral or parenteral administration to a subject. In still other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intrarectally, for example, as a pessary, cream or foam; or (5) aerosol, for example, as an aqueous aerosol, liposomal preparation or solid particles containing the compound.

The methods of the invention further include administering to a subject a therapeutically effective amount of an LRRK2 modulator compound in combination with a pharmaceutically acceptable excipient. The phrase "pharmaceutically acceptable" refers to those compounds of the invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable excipient" includes pharmaceutically-acceptable material, composition or vehicle, such as a liquid or solid filler, diluent, carrier, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing an LRRK2 modulator agent of the invention include those suitable for oral, nasal, topical (including buccal and sublingual), rectal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these compositions include the step of bringing into association a compound(s) with the carrier and, optionally, one or more accessory ingredients. In general, the formulations are prepared by uniformly and intimately bringing into association a compound with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants, such as wetting agents, emulsifying and suspending agents, sweetening, flavoring, coloring, perfuming and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal administration may be presented as a suppository, which may be prepared by mixing one or more compound(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum cavity and release the active agent.

Dosage forms for the topical or transdermal administration of a compound(s) include powders, sprays, ointments, pastes, creams, lotions, gels, solutions, patches and inhalants. The active compound(s) may be mixed under sterile conditions with a pharmaceutically-acceptable carrier, and with any preservatives, buffers, or propellants which may be required.

The ointments, pastes, creams and gels may contain, in addition to compound(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids, such as glycine, buffers, salts, sugars or sugar alcohols. Aerosols generally are prepared from isotonic solutions.

Transdermal patches have the added advantage of providing controlled delivery of a compound(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Pharmaceutical compositions of this invention suitable for parenteral administration comprise one or more compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of compound(s) in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

Pharmaceutical compositions according to the invention may be formulated to release the active compound substantially immediately upon administration or at any predetermined time or time period after administration. The latter types of compositions are generally known as controlled release formulations. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include for instance single or multiple unit tablet or capsule compositions, oil solutions, suspensions, emulsions, microcapsules, microspheres, molecular complexes, nanoparticles, patches, and liposomes. In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, Cold Spring Harbor Laboratory Press, New York.); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel et al., Wiley Interscience, New York, 2001)); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Kits

The disclosure also provides in other aspects kits for the treatment or prevention or monitoring of inflammatory bowel disease, including Crohn's disease and ulcerative colitis. In one embodiment, the kit includes a therapeutic or prophylactic composition containing an effective amount of an agent of the invention (e.g., a LRRK2 modulator) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, an agent of the disclosure is provided together with instructions for administering it to a subject having or at risk of developing a disease. The instructions will generally include information about the use of the composition for the treatment or prevention of the disease (e.g., Crohn's disease). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

It should be appreciated that the invention should not be construed to be limited to the examples that are now described; rather, the invention should be construed to include any and all applications provided herein and all equivalent variations within the skill of the ordinary artisan.

Example 1. Increased LRRK2 Levels Associated with the LRRK2 IBD Risk Polymorphism Results in Enhanced Pro-Inflammatory Responses and Experimental Colitis that is Reversed by LRRK2 Inhibition Mutations and single nucleotide polymorphisms (SNPs) in the LRRK2/MUC19 gene region are risk factors associated with several major diseases including Parkinson's disease (PD), inflammatory bowel disease (IBD) and leprosy. With respect to IBD, the SNP at rs11564258 in this locus is the third strongest genetic risk factor so far identified and thus its contribution to disease pathogenesis may hold a key to understanding disease mechanism and possible treatment.

In initial studies to evaluate how this SNP affected LRRK2 expression LRRK2 mRNA and protein levels were compared in eight lymphoblastoid cell lines that were heterozygous for the risk allele (G/A) at rs11564258 with gender- and ethnicity-matched control cells lacking a risk allele (G/G) at this locus; studies were limited to heterozygous cells since the frequency of the risk allele (A) is very low and homozygous A/A cells were unavailable. The heterozygous cells exhibited significantly increased LRRK2 mRNA and protein levels (FIGS. 1a and b) indicating that the risk allele was associated with increased LRRK2 levels even in individuals without intestinal inflammation. On the basis of this finding LRRK2 function was examined in C57BL/6J transgenic mice bearing a bacterial artificial chromosome expressing FLAG-tagged LRRK2 (LRRK2-Tg mice) and thus having increased LRRK2 expression.

Figure 2B:
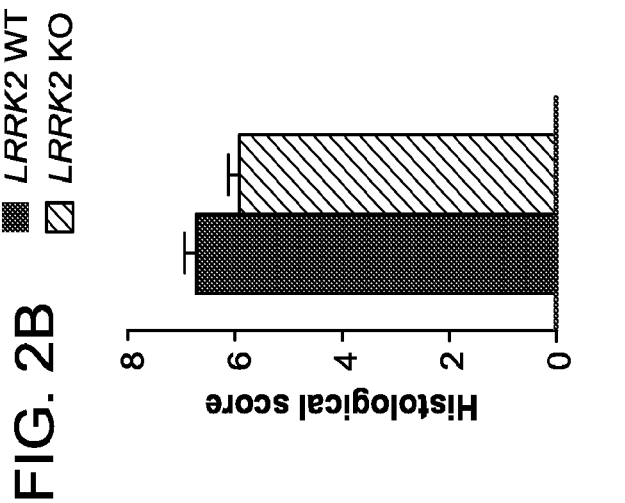
FIGS. 2a and 2b show the impact of LRRK2 knockout upon (a) % body weight over a seven day time course and (b) histological score. In contrast to results shown in FIG. 1a to FIG. 1c, DSS-colitis in LRRK2 KO mice was slightly less severe than in control mice (FIG. 2a and FIG. 2b).
Figure 2A:
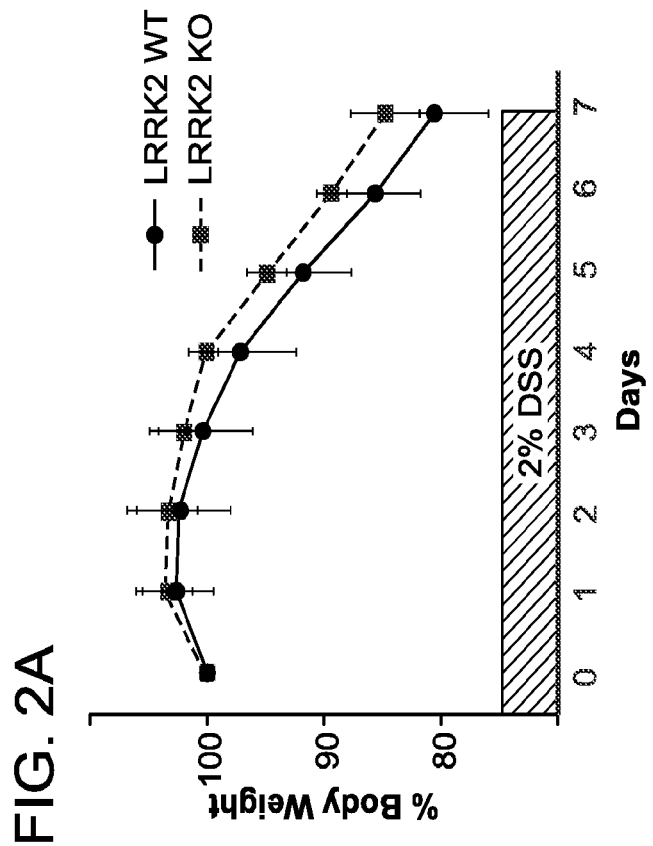

In initial studies to evaluate global LRRK2 function in bowel inflammation, LRRK2-Tg mice (as well as LRRK2 KO mice) were subjected to DSS (dextran-sulfate)-colitis. The transgenic mice did not display spontaneous colitis (in repeated studies) but did exhibit more severe DSS-colitis associated with enhanced pro-inflammatory cytokine secretion as compared with littermate control mice (FIG. 1c-FIG. 1f). In contrast, DSS-colitis in LRRK2 KO mice was slightly less severe than in control mice (FIG. 2a and FIG. 2b). This latter result differs from that reported by Liu et al. who found increased severity of DSS colitis in LRRK2 KO mice. This discrepancy is likely due to differences in the control mice used in the two studies: the experiments described herein used control mice that had been back-crossed for 9 generations, were housed in the same facility and exposed to the same microbiota. These studies of DSS-colitis thus indicate that increased expression of LRRK2 leads to an increased inflammatory response in experimental colitis.

Figure 3A:
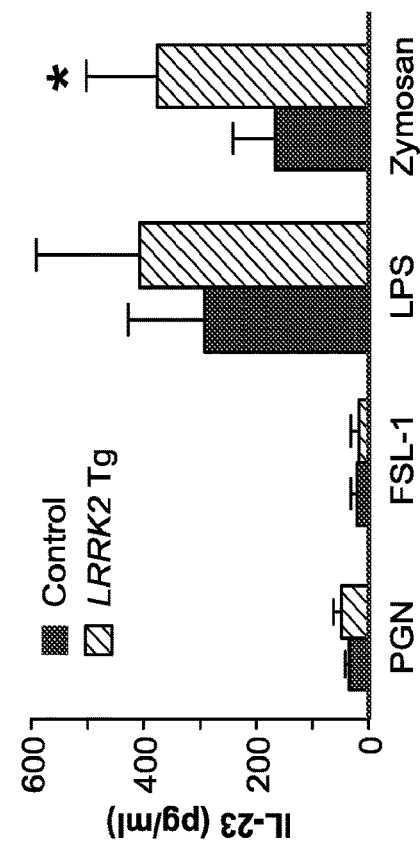
FIG. 3a to FIG. 3i show the results of experiments to define LRRK2 signaling pathways. Bone marrow-derived dendritic cells (BMDC) were stimulated from LRRK2-Tg and control mice with various TLR ligands. It was found that whereas TLR2 and TLR4 ligands did not elicit an increased response in transgenic mice compared to control mice, zymosan induced significant increases in both TNF-α and IL-23 synthesis (FIG. 3a and FIG. 3b). BMDC were also stimulated with yeast extract depleted of zymosan by treatment with hot alkali (ZymD), a Dectin-1 agonist that does not signal via TLRs, as well as heat-killed *Saccharomyces cerevisiae* (HK-SC) and heat-killed *Candida albicans* (HK-CA), other Dectin-1 agonists. It was found that these stimuli also induced increased TNF-α and IL-23 production by LRRK2-Tg BMDCs (FIG. 3c and FIG. 3d). In a final series of studies relating to LRRK2 down-stream interactions, it was found that LRRK2 binds to various components of the NF-kB activation complex including TRAF6, TAK1, TAB2 and NEMO (FIG. 3e and FIG. 3f); in addition, LRRK2 alone and synergistically with TRAF6 augmented K63-polyubiquitination of NEMO (FIG. 3g to FIG. 3i).
Figure 3B:
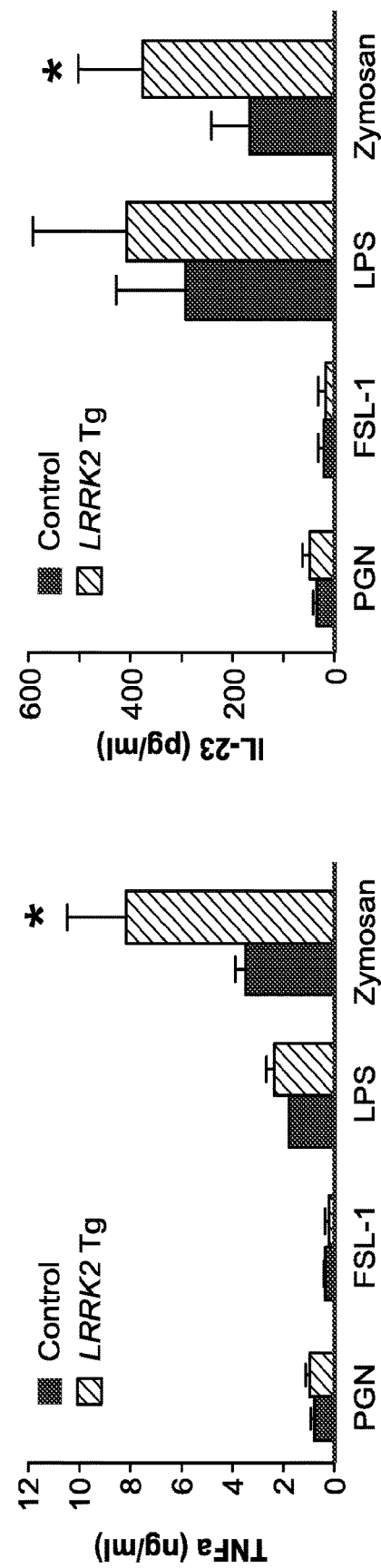
Figure 3C:
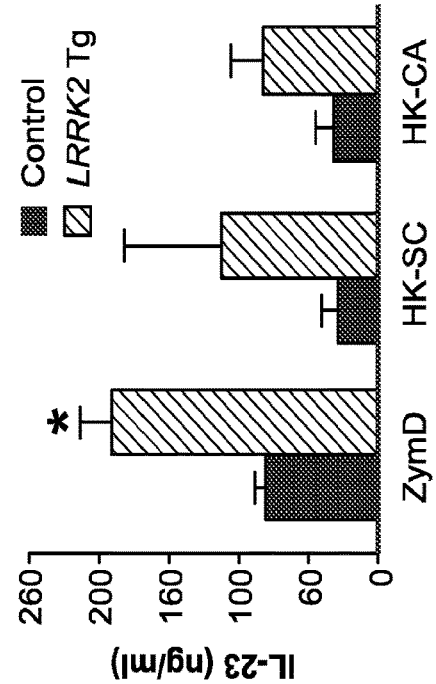
Figure 3D:
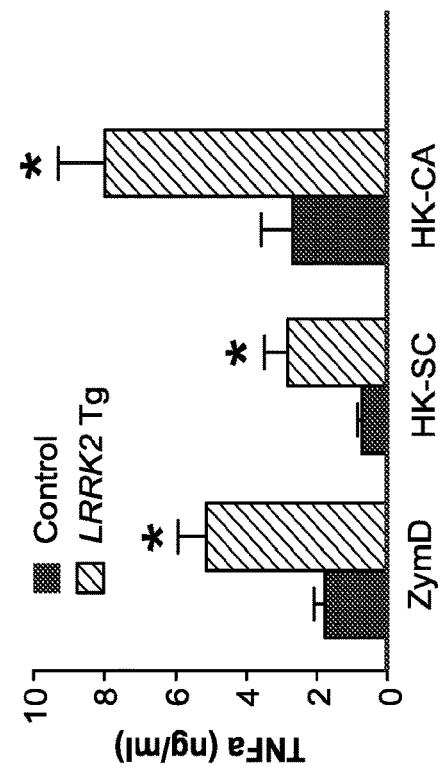

Since several of the candidate susceptibility genes in IBD (e.g., NOD2 and CARDS) are likely to be causing disease via an abnormal innate immune response, it was reasoned that increased LRRK2 expression was leading to an enhanced inflammatory response initiated by a Pathogen Associated Molecular Patterns (PAMPs) in the gastrointestinal environment. To examine this possibility bone marrow-derived dendritic cells (BMDC) were stimulated from LRRK2-Tg and control mice with various TLR ligands including zymosan, a yeast wall extract that also signals via Dectin-1, a beta-glucan receptor, and found that whereas TLR2 and TLR4 ligands did not elicit an increased response in transgenic mice compared to control mice, zymosan induced significant increases in both TNF-a and IL-23 synthesis (FIGS. 3a and b). To further define the increased responsiveness of LRRK2-Tg cells BMDC were stimulated with yeast extract depleted of zymosan by treatment with hot alkali (ZymD), a Dectin-1 agonist that does not signal via TLRs as well as other Dectin-1 agonists. Indeed, it was found that ZymD, as well as heat-killed *Saccharomyces cerevisiae* (HK-SC) and heat-killed *Candida albicans* (HK-CA), also induced increased TNF-α and IL-23 production in LRRK2-Tg BMDCs (FIG. 3c and FIG. 3d).

Figure 3E:
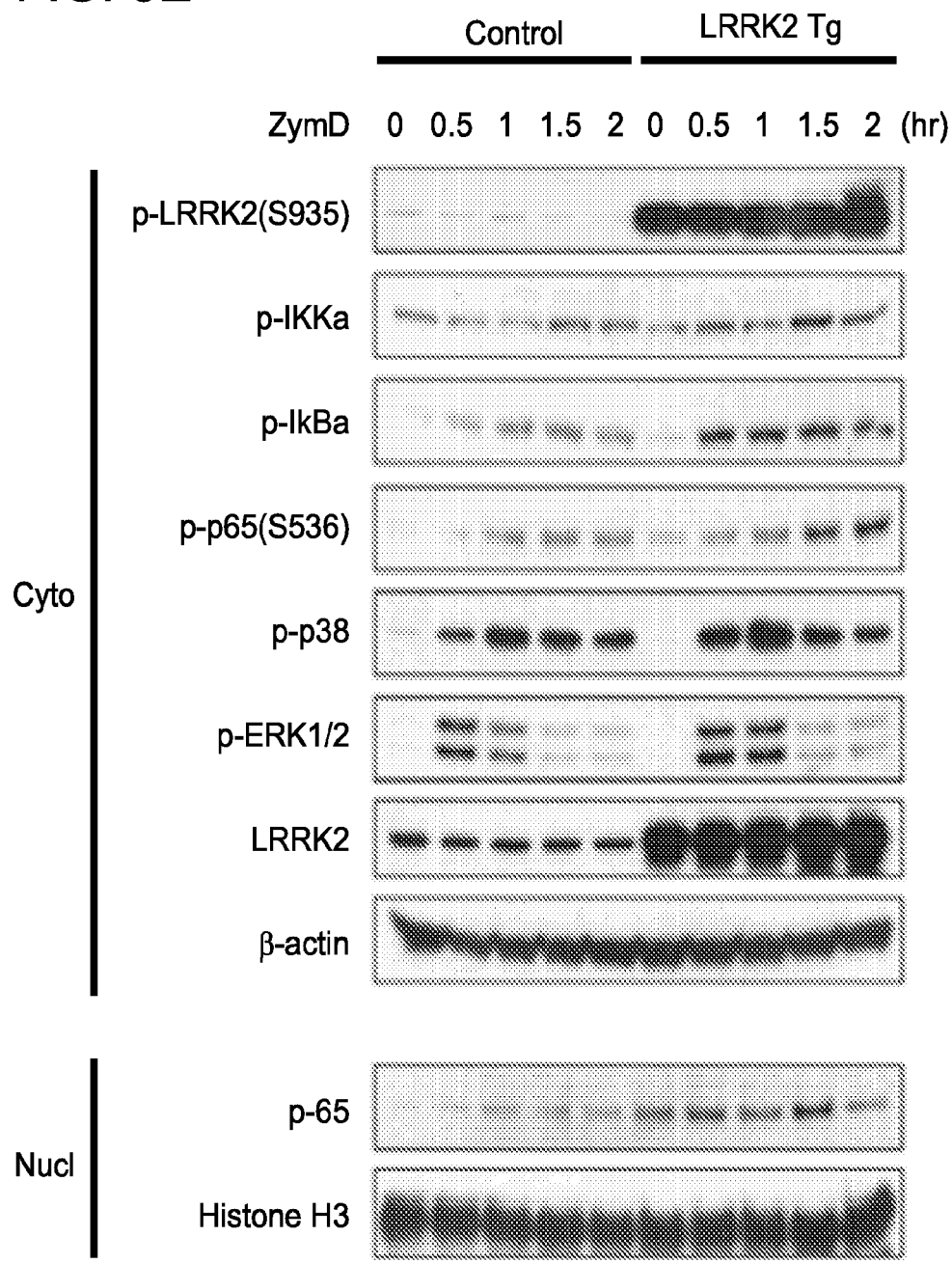
Figure 3F:
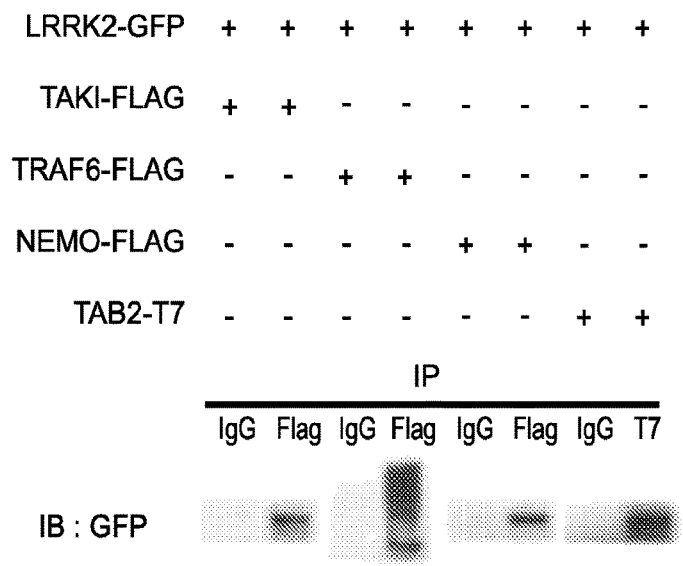
Figure 3G:
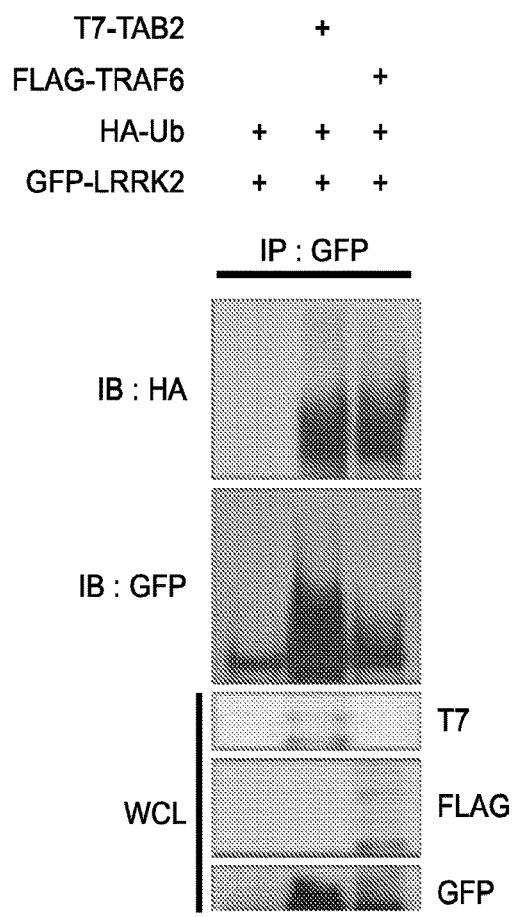
Figure 3H:
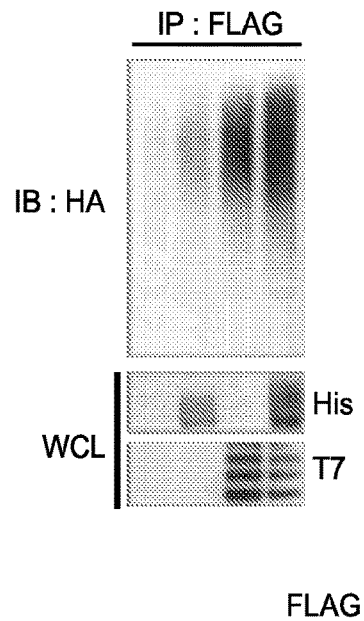
Figure 3I:
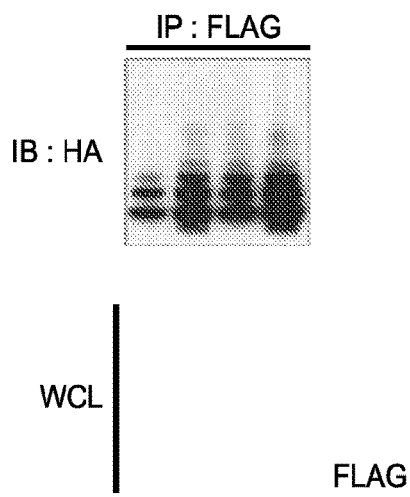

The augmented Dectin-specific induction of pro-inflammatory cytokines in LRRK2-Tg BMDC described above suggested a role of LRRK2 in NF-kB activation. To investigate this possibility first the down-stream binding partners of LRRK2 and their interactions were determined. In these studies HEK293T cells were transfected with an LRRK2-GFP-expressing vector along with one or more vectors expressing possible down-stream interacting molecules and then subjected cell extracts to immunoblotting. It was found that LRRK2 binds to various components of the NF-kB activation complex including TRAF6, TAK1, TAB2 and NEMO (FIG. 30. Since TRAF6 is an E3 ubiquitin ligase that mediates Lys-63 (K63)-linked polyubiquitination and activation of interacting molecules, the ubiquitination status of LRRK2 following its binding to TRAF6 was next determined with blotting studies in which complexes were identified with anti-HA ubiquitin. It was found that LRRK2 interaction with TRAF6 or with TRAF6 and TAB2 results in robust LRRK2 K63-linked polyubiquination. Somewhat unexpectedly, it was also found that LRRK2, particularly in the presence of TAB2, induces TRAF6 K63-linked polyubiquitination, suggesting that LRRK2 interaction with down-stream components initiates a positive polyubiquitination feedback loop. In a final series of studies relating to LRRK2 downstream interactions it was tested whether LRRK2 interacts with NEMO, the proximal regulator of NF-kB activation and found that LRRK2 alone and synergistically with TRAF6 augments K63-polyubiquitination of NEMO (FIG. 3f to FIG. 3i). These interactions, taken together, set the stage for NF-kB activation and indeed it was found that ZymD stimulation of BMDC from LRRK2 Tg mice positively regulates NF-kB-related components (IKKa, IkBa and p65) and, to a lesser extent, activates MAP kinase related molecules (p38 and ERK1/2) (FIG. 3e). Thus, the increased ZymD induction of pro-inflammatory cytokines in LRRK2-Tg BMDC can be explained by the effect of LRRK2 on NF-KB signaling.

Previous studies of LRRK2 in relation to Parkinson's disease have shown the overexpression of LRRK2 with two different coding mutations or, paradoxically, knock-down of LRRK2 exhibit increases neural tissue autophagic function. This raised the question of whether the IBD-associated LRRK2 polymorphism and associated increase in LRRK2 expression also affected autophagy.

Figure 4A:
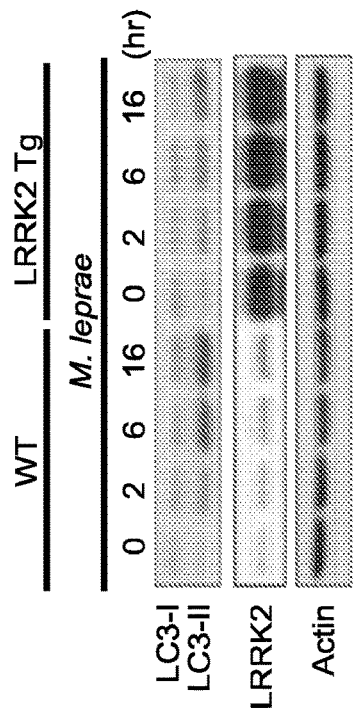
Figure 4C:
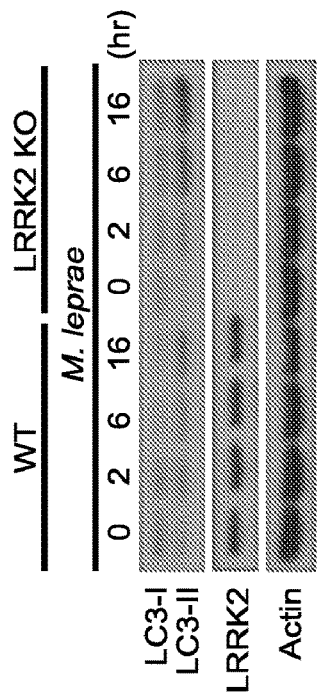
Figure 4B:
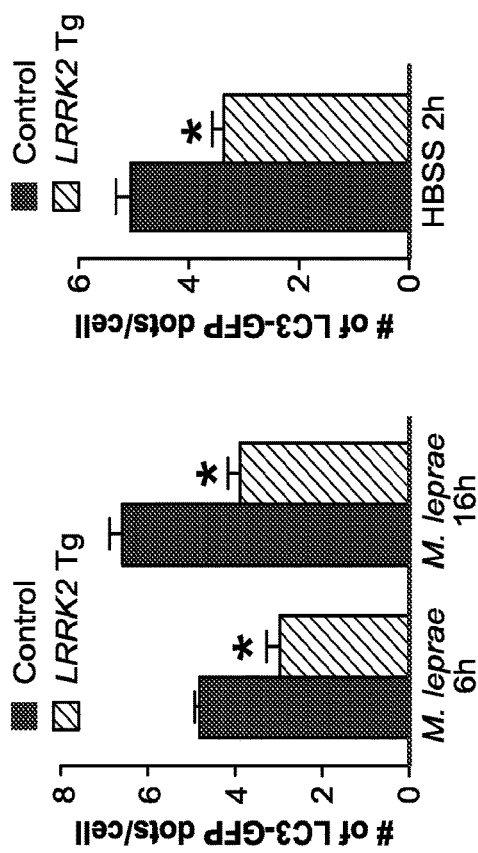
Figure 4D:
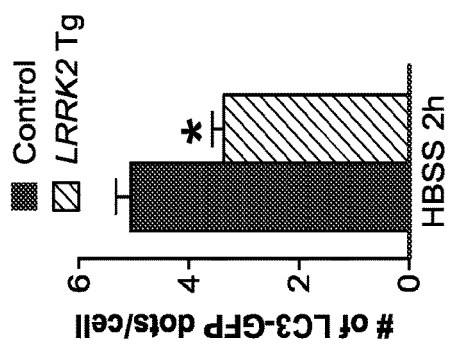
Figure 4D:
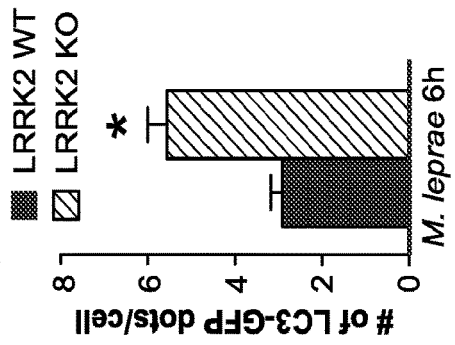

In initial studies addressing this question, BMDC were stimulated with irradiated *M. leprae* (*M leprae*) or ZymD and found in Western blot studies that LC3-II conversion, a marker of the induction of autophagy, is increased in LRRK2-KO (FIG. 4a) and decreased in LRRK2-Tg BMDC (FIG. 4b) compared to control mice. This finding was then verified with studies of *M. leprae-* or ZymD-stimulated BMDCs from LRRK2 KO or LRRK2 Tg mice bearing an LC3-GFP gene that thus allowed the quantitation of the development of autophagy-associated LC3 puncta. It was found that LRRK2 KO cells exhibited increased numbers of LC3 puncta and cells from LRRK2 Tg exhibited decreased numbers of LC3 puncta (FIG. 4c and FIG. 4d). These results thus indicated that increased LRRK2 expression inhibited autophagy in dendritic cells.

Figure 4E:
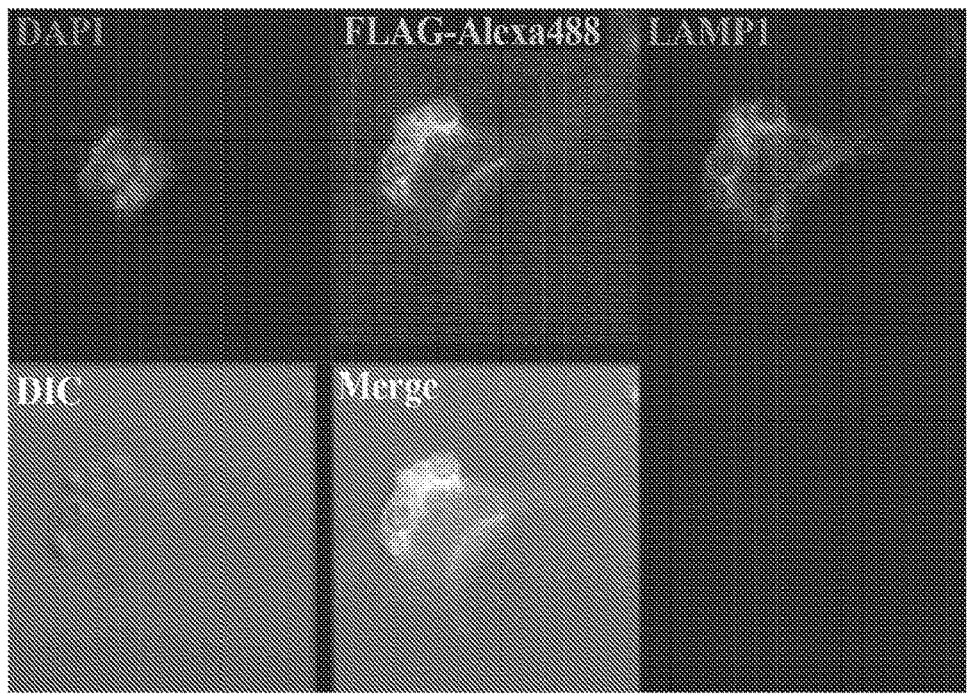
Figure 4F:
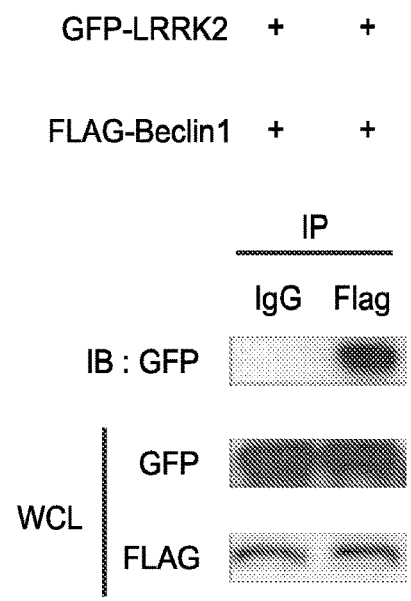

In studies of the mechanism of LRRK2 inhibition of autophagy it was first determined if LRRK2 associates with an endosomal membrane, the usual location of autophagy-associated proteins following stimulation of BMDCs with a phagosome-inducing stimulus. It was found that after such stimulation with HK-CA, LRRK2 co-localizes with endosomal/lysosomal membrane marker, LAMP1 (FIG. 4e). Next it was determined if LRRK2 interacts with Beclin-1, a key initiator of the autophagy cascade that has previously been shown to be inhibited by TAB2, an LRRK2 interacting molecule. It was found that LRRK2 does, in fact, bind to Beclin-1; in addition, using a Proximity Ligation Assay (in situ PLA) it was demonstrated that whereas in unstimulated BMDC uncomplexed LRRK2 is found in the cytosol or on vesicular membranes, in HK-CA-stimulated BMDC the LRRK2/Beclin-1 complex can be found on an endosomal membrane (FIG. 4g).

Figure 4H:
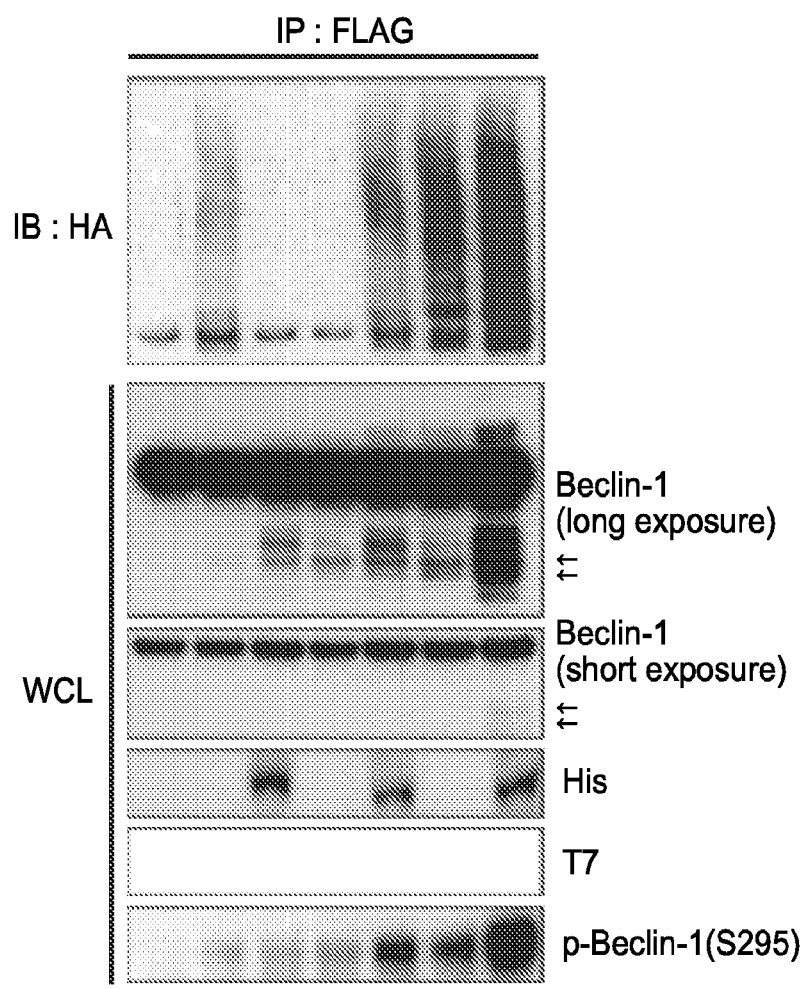

In a final series of studies relating to LRRK2 inhibition of autophagy the mechanism of LRRK2-induced Beclin inactivation was examined. It has been shown that Beclin-1 can be degraded and inactivated by caspase 3 and 8 in a process that results in cleaved Beclin-1 bands. To determine if LRRK2 in association to TAB2 promotes Beclin-1 degradation, HEK293T cells were transfected with vectors expressing LRRK2, TAB2 and K48-ubiquitin alone or in combination and then analyzed immunoblots for Beclin-1 degradation bands and K48-polyubiquitination. It was found that LRRK2 transfection alone and in synergy with TAB2 transfection gave rise to Beclin-1 degradation bands and K48 polyubiquitination bands (FIG. 4h and FIG. 4i). A second or concomitant mechanism of Beclin-1 inactivation consists of Akt-mediated phosphorylation of this molecule at S234 and S295. It was found that either LRRK2 or TAB2 induced phosphorylation at S295 and that these components synergistically increased such phosphorylation (FIG. 4j).

Figure 5C:
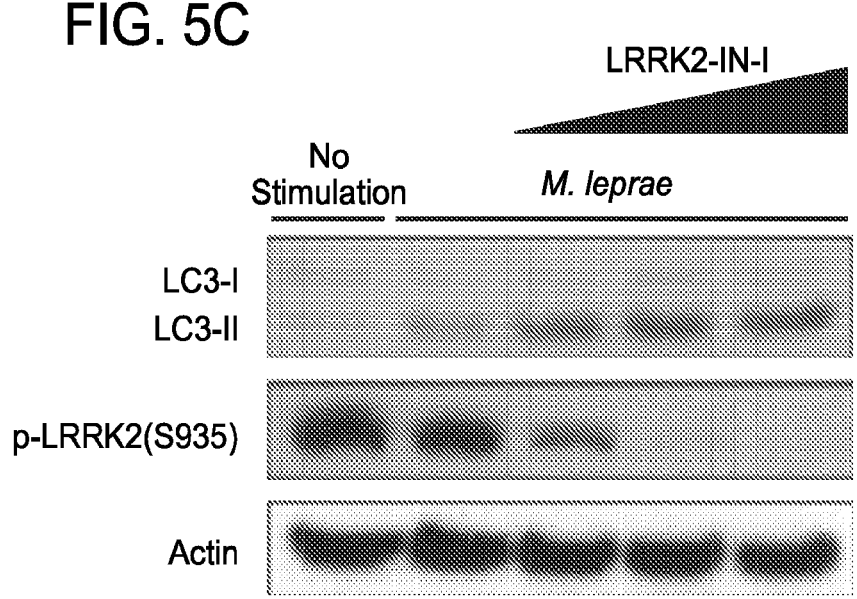
Figure 5D:
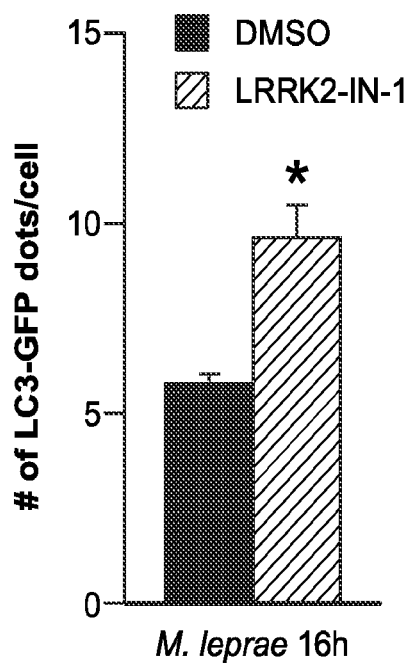
Figure 5E:
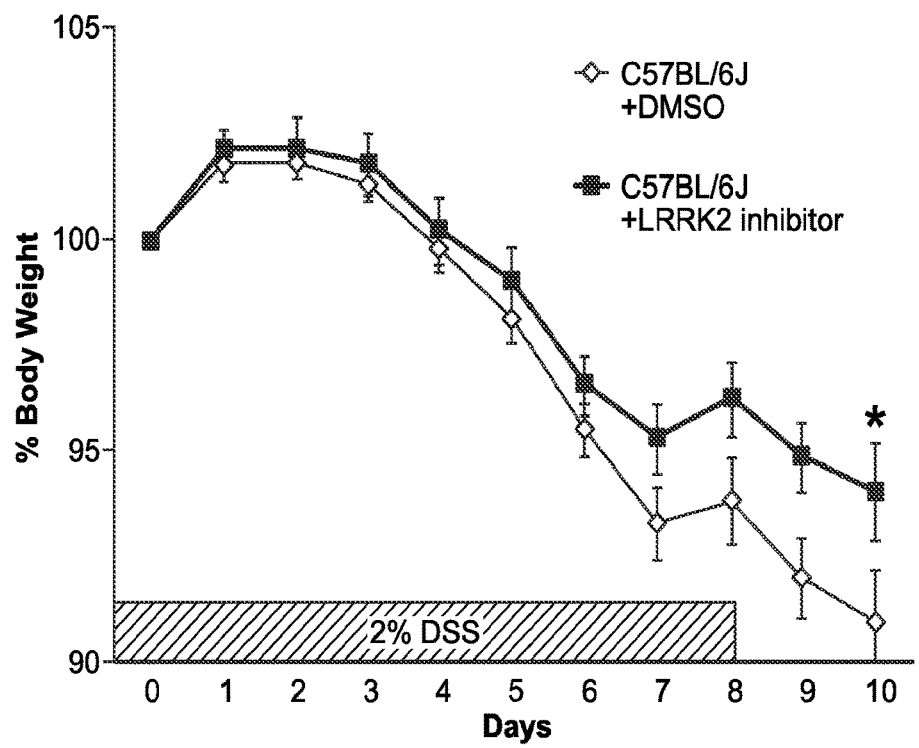
Figure 5F:
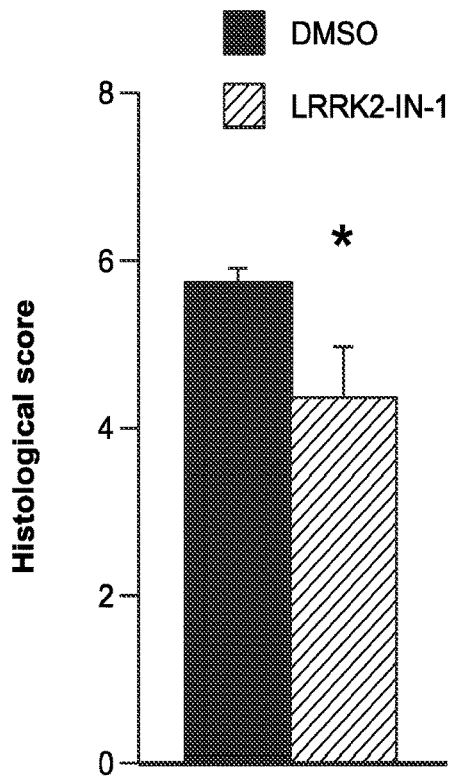

LRRK2 inhibitors have proven to provide protection from the development of LRRK2-induced neurodegeneration in both in vitro and in vivo models of PD and are thus potential therapeutic agents for this disease. Furthermore, in rat microglia, LRRK2 inhibitors block TLR4-induced TNF-a and iNOS production. Based on these findings, whether LRRK2 inhibition can serve as a therapeutic target in IBD was investigated. First, ZymD-induced cytokine production in BMDC from LRRK2 Tg mice in the presence or absence of two LRRK2 inhibitors, LRRK2-IN-1 and CZC54252. Both inhibitors suppressed the production of a wide range of pro-inflammatory cytokine mRNAs, including TNF-alpha, TL1A, IL-23p19, IL-6 and IL-1beta mRNAs and the inhibition of TNF-alpha was dose dependent (FIG. 5a and FIG. 5b). In addition, cultures of human BMDC derived from Crohn's disease peripheral blood also exhibited suppressed TNF-alpha production induced by ZymD both at the transcriptional and protein levels in the presence of inhibitor (FIG. 5c). Next, the effect of a LRRK2 inhibitor on autophagy was investigated, and it was found that both by Western blotting and by quantitation of LC3 puncta that LRRK2-IN-1 reversed inhibition of autophagy in M. leprae- and ZymD-stimulated BMDC from LRRK2 Tg mice (FIG. 5d and FIG. 5e).

The above in vitro studies indicated that NF-1d3 activation and inhibition of autophagy caused by LRRK2 in LRRK2 Tg mice could be restored by the modulation of LRRK2 activity. It was thus determined if an LRRK2 inhibitor could reverse the increased intensity of DSS-colitis in mice, and it was found that administration of LRRK2In-1 to wild-type mice did indeed ameliorate the increased DSS-colitis in such mice.

Example 2. Therapeutic Administration of an LRRK2 Inhibitor to Crohn's Disease and Ulcerative Colitis Patient Populations The LRRK2 inhibitor LRRK2-IN-1 is formulated for administration to a patient population having inflammatory bowel disease, specifically including subjects having CD and/or UC. Formulated LRRK2-IN-1 is administered to each subject at the equivalent in the subject of a concentration in the environment of a target cell of, e.g., 0.1 µM, 1 µM and 10 µM, or other dose determined by initial range-finding studies. Single dose and/or multi-dose administrations are performed, and the impact of such administrations are assessed at an appropriate interval post-administration.

Evaluation of the impact of LRRK2-IN-1 upon subjects having CD and/or UC is performed by assessing one or more of the following in the subjects: comparison of exemplary symptoms of CD, e.g., diarrhea, abdominal pain and cramping, bloody stool, ulcer, reduced appetite/weight loss, fever, fatigue, arthritis, eye inflammation, mouth sores, skin disorders, inflammation of the liver or bile ducts and/or delayed growth or sexual development (pediatric studies) to an appropriate control subject; comparison of exemplary symptoms of UC, e.g., ulcerative proctitis, proctosigmoiditis, left-sided colitis, pancolitis and/or fulminant colitis to an appropriate control subject; and evaluation of molecular markers of inflammation (e.g., pro-inflammatory cytokines and NF-kB as disclosed above) for inhibition in treated subjects as compared to an appropriate control subject. The therapeutic impact of LRRK2-IN-1 upon CD and UC is thereby assessed. Other candidate inhibitors of LRRK2 can also be assessed in the same manner.

INCORPORATION BY REFERENCE

All patents, publications, CAS numbers, and accession numbers mentioned in this specification are herein incorporated by reference to the same extent as if each independent patent and publication was specifically and individually indicated to be incorporated by reference.

What is claimed is:

1. A method of treating an inflammatory bowel disease (IBD) associated with overexpression or increased activity of leucine rich repeat kinase 2 (LRRK2), the method comprising:
   administering to a subject an inhibitor of LRRK2 in an amount effective to treat the intestinal disease or disorder,
   wherein the inhibitor of LRRK2 is effective at treating the IBD.

2. The method of claim 1, wherein the inflammatory bowel disease is ulcerative colitis.

3. The method of claim 1, wherein the inflammatory bowel disease is Crohn's disease.

4. The method of claim 1, wherein the LRRK2 inhibitor is selected from the group consisting of: peptides or polypeptides, small molecules and nucleic acid inhibitors.

5. The method of claim 4, wherein the polypeptide is an antibody, or antigen-binding fragment thereof.

6. The method of claim 4, wherein the LRRK2 inhibitor is selected from the group consisting of: LRRK2-IN-1, CZC54252, GSK2578215, GSK429286A, GSK269962A, HG-10-102-01, GNE-7915, CZC-25146, TAE684, indirubin-3-monoxime, sunitinib, GW5074, H-89, fasudil, hydroxyfasudil, H-1152, and Y-27632.

7. The method of claim 1, wherein the LRRK2 modulator is administered in combination with an additional agent.

8. The method of claim 7, wherein the additional agent is selected from the group consisting of: anti-inflammatory agents, immunomodulators, antibiotics and non-steroidal anti-inflammatory drugs.

9. The method of claim 1, wherein the method includes a step of providing the subject determined to have overexpression or increased activity of LLRK2 prior to administering an inhibitor of LRRK2.

10. The method of claim 1, wherein the subject is determined to have single nucleotide polymorphism (SNP) rs11564258.

11. A method of treating Crohn's disease or ulcerative colitis, the method comprising:
   administering to a subject an inhibitor of LRRK2 in an amount effective to treat the intestinal disease or disorder, wherein the inhibitor of LRRK2 is effective at treating the Crohn's disease or the ulcerative colitis.

12. The method of claim 11, wherein the LRRK2 inhibitor is selected from the group consisting of: peptides or polypeptides, small molecules and nucleic acid inhibitors.

13. The method of claim 12, wherein the polypeptide is an antibody, or antigen-binding fragment thereof.

14. The method of claim 12, wherein the LRRK2 inhibitor is selected from the group consisting of: LRRK2-IN-1, CZC54252, GSK2578215, GSK429286A, GSK269962A, HG-10-102-01, GNE-7915, CZC-25146, TAE684, indirubin-3-monoxime, sunitinib, GW5074, H-89, fasudil, hydroxyfasudil, H-1152, and Y-27632.

15. The method of claim 1, wherein the LRRK2 modulator is administered in combination with an additional agent.

16. The method of claim 15, wherein the additional agent is selected from the group consisting of: anti-inflammatory agents, immunomodulators, antibiotics and non-steroidal anti-inflammatory drugs.

17. The method of claim 11, wherein the method includes providing the subject determined to have overexpression or increased activity of LLRK2 prior to administering an inhibitor of LRRK2.

18. The method of claim 11, wherein the subject is determined to have single nucleotide polymorphism (SNP) rs11564258.

* * * * *